United States Patent [19]

Causey, III et al.

[11] Patent Number: 4,809,697
[45] Date of Patent: Mar. 7, 1989

[54] INTERACTIVE PROGRAMMING AND DIAGNOSTIC SYSTEM FOR USE WITH IMPLANTABLE PACEMAKER

[75] Inventors: James D. Causey, III, Simi Valley; Harold C. Schloss, Los Angeles; Jeffery D. Snell, Northridge, all of Calif.

[73] Assignee: Siemens-Pacesetter, Inc., Sylmar, Calif.

[21] Appl. No.: 108,842

[22] Filed: Oct. 14, 1987

[51] Int. Cl.[4] .......................... A61N 1/00; H05G 00/00
[52] U.S. Cl. ............................... 128/419 PT; 128/903
[58] Field of Search ................... 128/419 PT, 419 PG, 128/630, 631, 697, 903

[56] References Cited

U.S. PATENT DOCUMENTS 4,476,869 10/1984 Bihn ............................... 128/419 PT
4,543,953 10/1985 Slocum et al. ................. 128/419 PT
4,559,947 12/1985 Renger et al. ................. 128/419 PG

*Primary Examiner*—Francis J. Jaworski
*Assistant Examiner*—George Manuel
*Attorney, Agent, or Firm*—Bryant R. Gold; Leslie S. Miller

[57] ABSTRACT

An analyzer-programmer system (30) for use with an implantable medical device, such as a cardiac pacemaker (20). The system facilitates non-invasive communications with the implantable device and makes analysis of the operation of the implantable device easier to understand and perform. The system includes conventional processor means (42) for processing a sequence of stored instructions stored in programmable read-only memory, or ROM (40). The ROM, although designed to be accessed through predefined page of information, and blocks within such pages, is configured to allow in-page addressing within any of a plurality of pages in a linear fashion. Programmed intervals to be sent to the implantable device are displayed by the system in tabular form or as scaled time-lines or bars (FIG. 9A), with each separate interval beginning and ending in proper timed sequence, thereby providing a prediction of the expected performance. Such programmed intervals can overlay or sidelay measured performance (FIG. 9B), thereby facilitating a comparison between predicted and measured performance. The system also includes telemetry head means (28) for sending and receiving control and data signals to and from the implanted medical device (20). The telemetry head means (28) includes processing circuitry (FIG. 4C) that greatly simplifies the other circuitry needed in order to effectuate such communication.

14 Claims, 12 Drawing Sheets

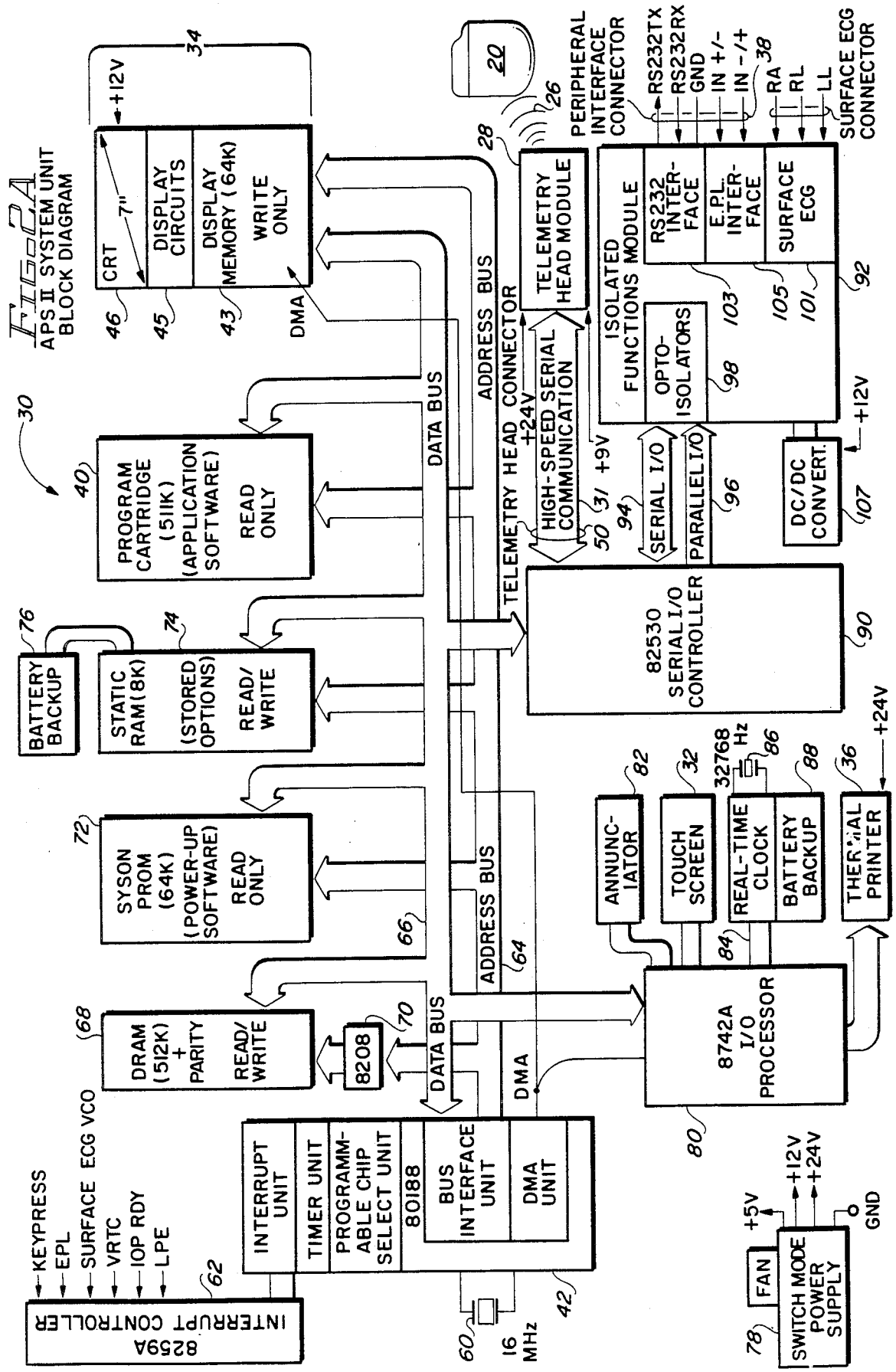

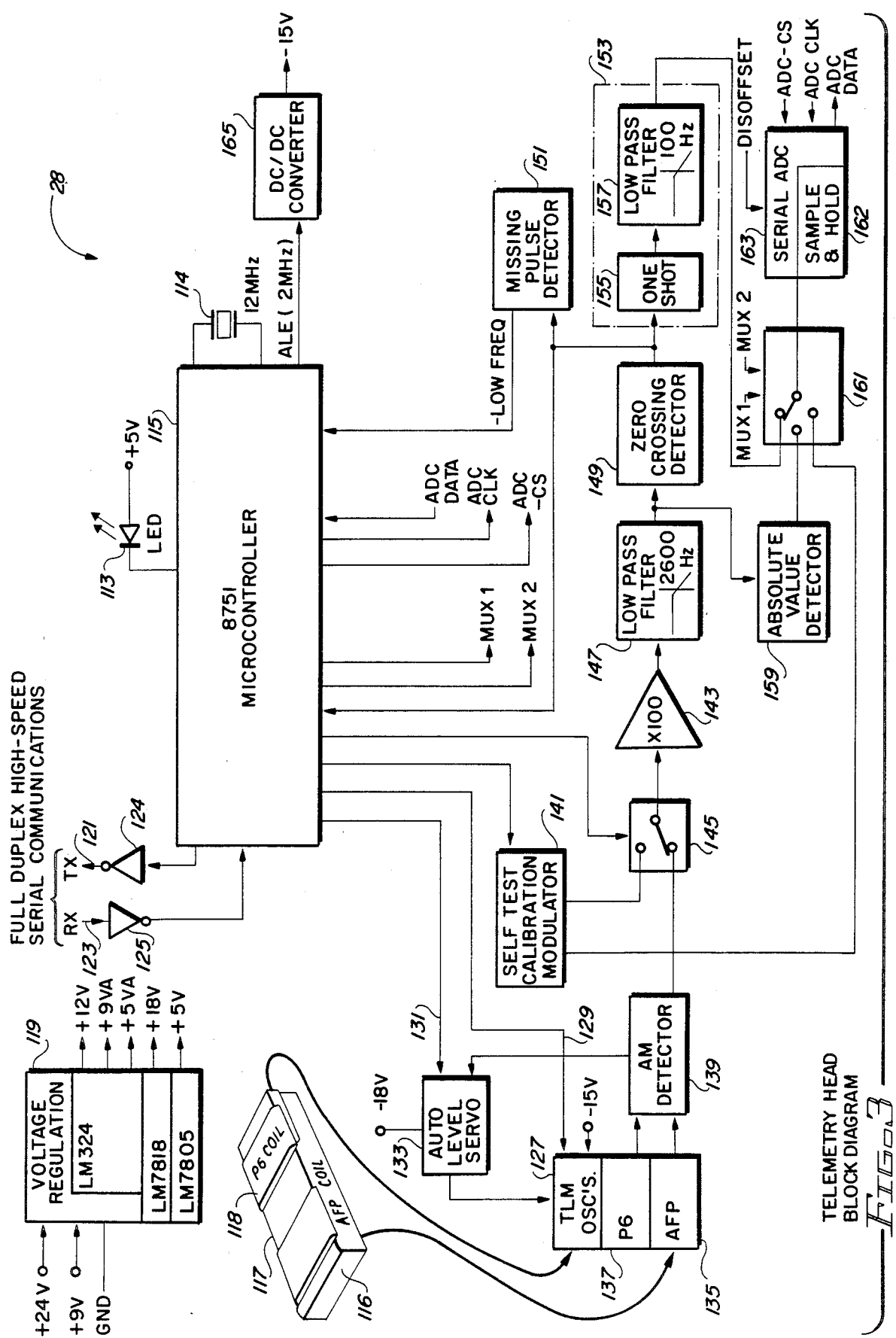

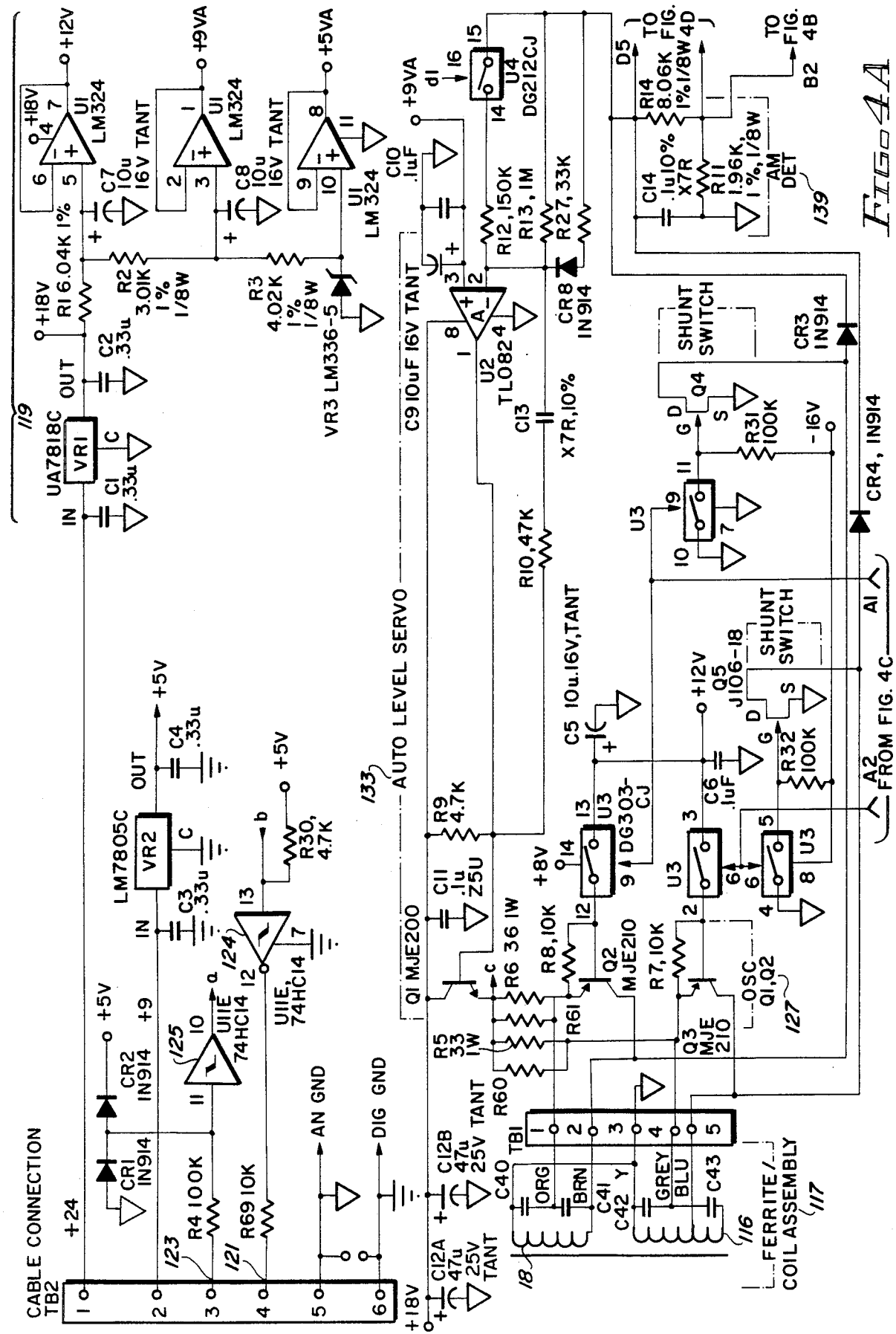

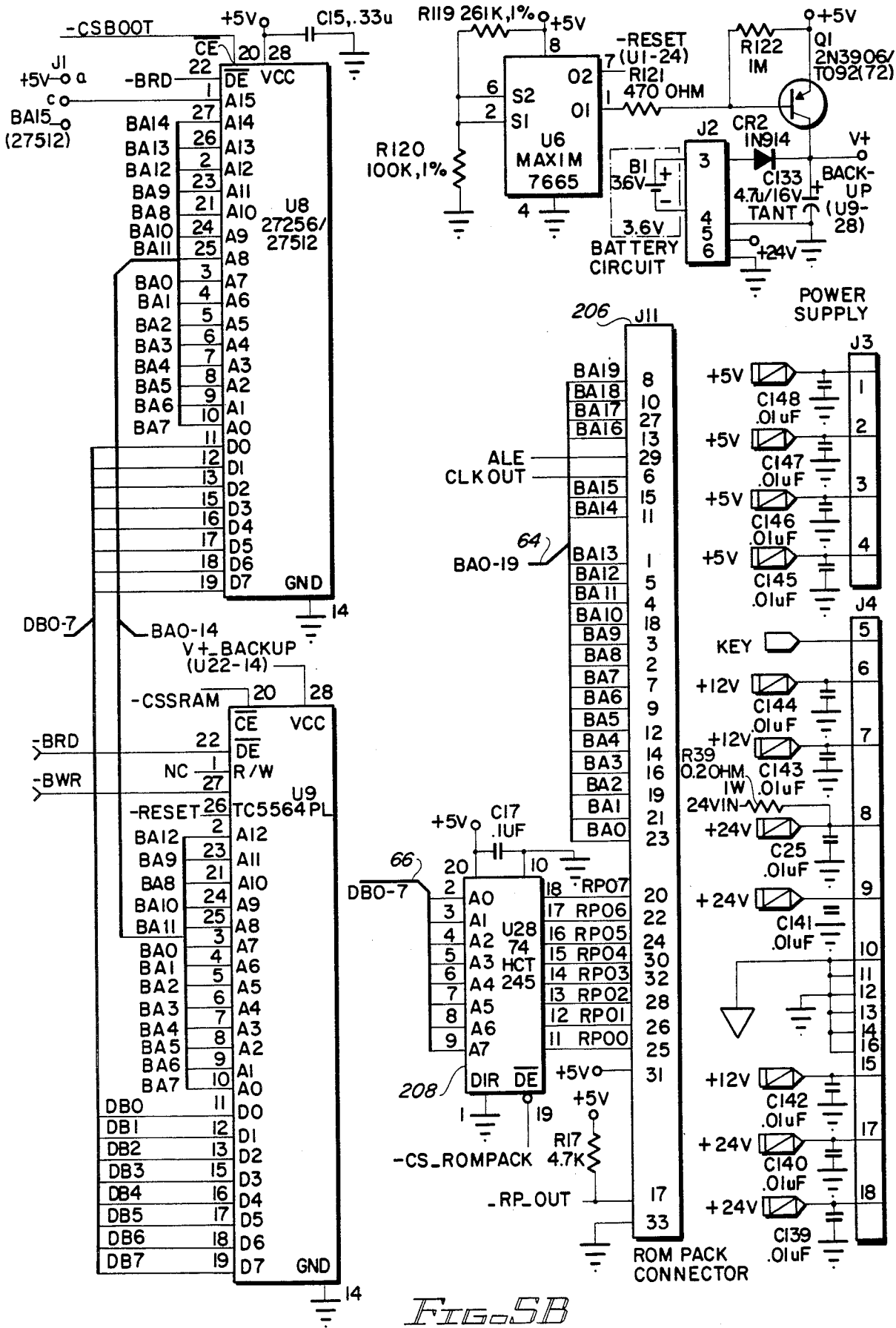

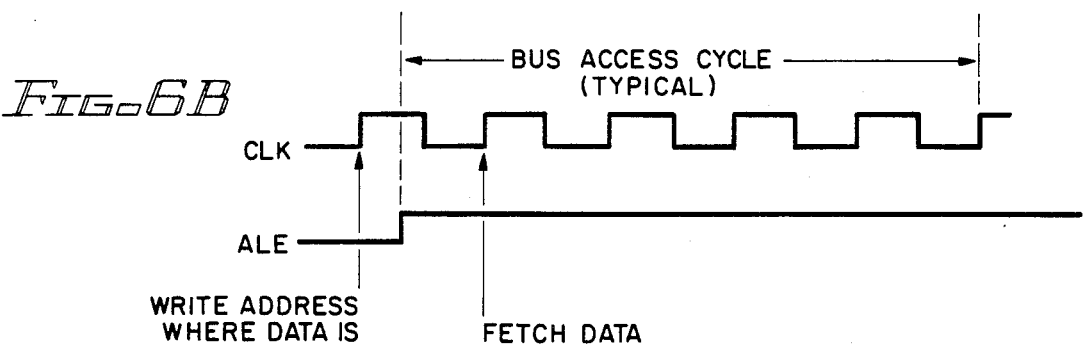
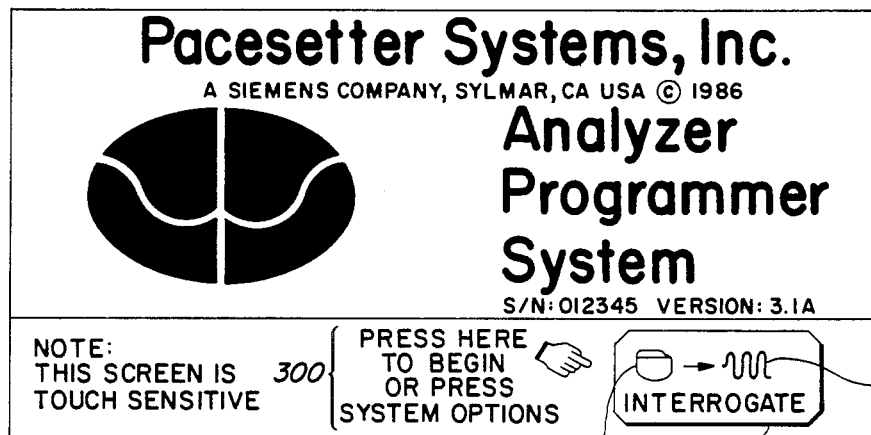
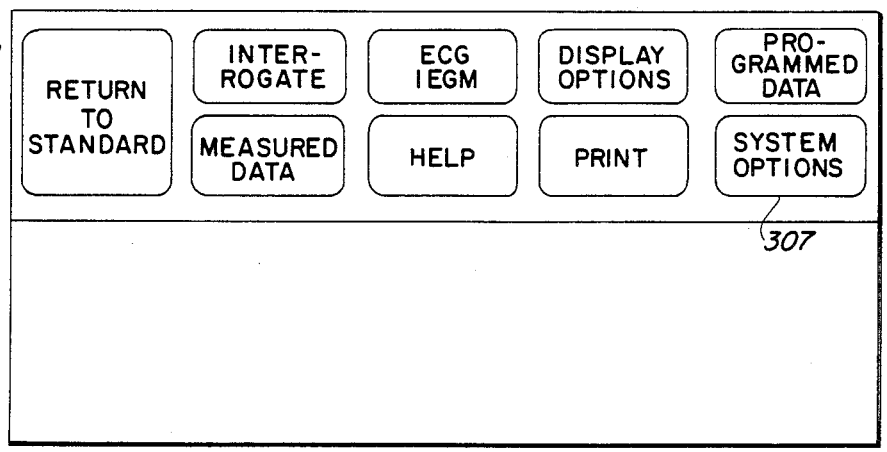
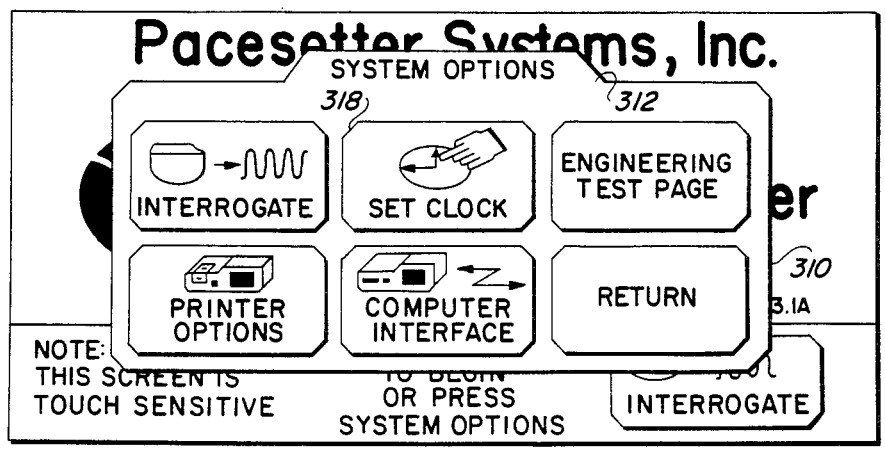

INTERACTIVE PROGRAMMING AND DIAGNOSTIC SYSTEM FOR USE WITH IMPLANTABLE PACEMAKER

BACKGROUND OF THE INVENTION

The present invention relates to programming/diagnostic devices for use with implantable programmable medical devices, such as pacemakers. More particularly, the present invention relates to specific improvements of pro-programming/diagnostic devices that (i) facilitate noninvasive communications with an implantable programmable pacemaker, and (ii) permit both real-time and prospective analysis of the pacemaker operation as it interacts with the heart.

In the past, the primary source of diagnostic data for use in analyzing the operation of an implanted pacemaker has been the surface electrocardiogram (ECG), in which both pacemaker and heart activity are blended. From the ECG, the activity of the heart—including the contraction of the atria, the contraction of the ventricles, and the timing therebetween—could be displayed. From the pacemaker, the activity of the pacemaker—including when a heart contraction was sensed and when a stimulating pulse was generated—could likewise be monitored through the use of marker signals telemetered from the pacemaker to a remote (non-implanted) receiver, where such signals were processed and displayed as marks on the ECG waveform.

In recent years, some implantable pacemakers have included the capability of transmitting an intercardiac ECG signal, either alone or in combination with marker signals, thereby allowing a complete analysis of the interaction of the heart with the pacemaker without the need of first obtaining surface ECG signals. See, e.g., U.S. Pat. No. 4,559,947. Pacesetter Systems, Inc., of Sylmar Calif., has in recent years provided a programming system for use with implanted pacemakers called an Analyzer-Programmer System (APS). The APS, when noninvasively coupled to an implanted pacemaker, and when also connected to conventional skin ECG electrodes, is capable of selectively displaying either the surface ECG or the intercardiac ECG with event and timing annotation of pacemaker activity. U.S. Pat. No. 4,596,255 describes some of the display and processing features of the APS. These features have greatly enhanced the ability to properly diagnose the interaction between pacemaker and patient. That is, by using an APS, a doctor, cardiologist, or other diagnostician can readily decipher the source of stimulating pulses, the response or lack of response of the heart to such pulses, the existence and duration of refractory periods, and the like. Such capability has proven especially useful in understanding and analyzing the complex operation of dual chamber pacemakers.

Unfortunately, while the APS and similar programming/diagnostic systems, such as those described in U.S. Pat. Nos. 4,208,008, 4,417,306, and 4,505,276, have done much to facilitate communications with and analysis of implantable programmable pacemakers, such systems typically require extensive training and experience on the part of their users before they can be used effectively. Like many microprocessor-based systems (e.g. personal computers), such systems can at times be very frustrating for the user unless the user is intimately familiar with the correct sequence of instructions that must be provided to invoke a desired response.

Moreover, where the principal operating parameters of the pacemaker are programmable (as is the case with most modern pacemakers), and particularly where the operation of a dual chamber pacemaker is being analyzed (a dual chamber pacemaker is one that is capable of sensing and/or pacing in both chambers of the heart), it has often been difficult for the user of the programming/analyzer system to know what the reaction of the heart will be or should be to a given programming change. This is because of the relatively large number of variables that can be involved in dual chamber pacing, each variable having potential of interacting with the others in affecting the overall operation of the pacemaker. With such a large number of variables, it is difficult for the user of the system to keep track of all possible interactions. Similarly, even when the programming/analyzer system provides or displays needed information, such as the values of selected variables or parameters, such information has not always heretofore been provided or displayed in a format that makes it easy to understand and use in relation to other known information.

Further, as the amount of information being transferred between such programmer/analyzer systems and the pacemaker has increased, the complexity, and hence the cost, of such systems has also increased. In some instances, the cost of such systems may be prohibitive, thereby necessitating the use of less complex programmer/analyzer systems that do not offer the full capabilities that are technologically available with the more complex programmer/analyzer systems.

What is needed therefore, is a programmer/analyzer system for use with implantable programmable pacemakers that offers all needed communication and diagnostic capabilities, yet is easy to use and understand, and is less costly to build. The present invention addresses these and other needs.

SUMMARY OF THE INVENTION

The present invention provides enhancements for an analyzer-programmer system used with implantable medical devices. In general, these enhancements facilitate communications with the implantable device and make analysis of the operation of the implantable device easier to understand and perform.

The invention relates not only to the analyzer-programmer system itself, including the manner in which read-only-memory (ROM) devices are used within the system, and the nature and character of displays and command-entering features that are available, but also to a time-interval programming system for use with an implantable medical device. Further, the invention is directed to a telemetry head module that forms part of the analyzer-programmer system, which telemetry head module provides a more efficient communication link between the implantable device and the main processor of the analyzer-programmer system.

The analyzer-programmer system of the present invention includes telemetry head means for sending and receiving control and data signals to and from an implanted medical device; processing means for generating the control signals in response to commands entered therein and for processing the data signals received from the telemetry head means; memory means for storing data signals; command-entering means for entering commands into the processing means, and display means for graphically displaying the information contained in both the control signals and data signals, the information contained in the control signals being displayable, in one embodiment, as a set of graphical programmed time-intervals, as described below.

The telemetry head means of the present invention is realized with a telemetry module that includes: (1) transceiver means for receiving and transmitting data and control signals from and to an implantable medical device; (2) digital data port means for receiving and sending digital data; and (3) processing means for modulating and conditioning the digital control signals received through the digital data port means and presenting the resulting modulated and conditioned control signals to the transceiver means, and for demodulating and conditioning the data signals received through the telemetry means and presenting the resulting demodulated and conditioned data signals as digital data to the digital data port means. Advantageously, such a configuration provides a much more efficient transfer of data and commands between the analyzer-programmer system and the implanted pacemaker than has heretofore been available.

The memory means of the present invention is made up of both conventional ROM and RAM devices, and further includes a unique ROM addressing scheme that permits direct in-page addressing of ROM data without the use of additional software. The result is a much more efficient retrieval of the data from the ROM. Using such a ROM addressing scheme, the addressed data is available on a data bus within a fraction of a clock cycle subsequent to the enabling of an address latch. This is in contrast to conventional ROM addressing schemes wherein the addressed data is typically not available on the data bus until after several clock cycles subsequent to the enabling of an address latch.

The display means of the present invention includes programmed time-interval display means for displaying a graphical or tabular representation of the programmed time intervals associated with the operation of the implanted pacemaker. A graphical programmed interval display depicts programmed intervals as scaled lines or bars, with each separate interval beginning and ending in proper time sequence relative to a time-line axis. Such a graphical display advantageously allows a programmer to quickly and easily understand and visualize the interaction between the implantable device and the body functions it monitors and/or controls (e.g., between an implanted pacemaker and the heart). Thus, a graphical programmed interval display provides a representation of the expected performance (i.e., a prediction of the performance) that will result from a particular set of programmed intervals. In one embodiment, such a graphical programmed interval display or equivalent may optionally overlay or sidelay a similar graphical display of measured real-time data, thereby facilitating a comparison between predicted and measured performance.

The time-interval programming means includes: (1) means for entering commands into the analyzer-programming system that are non-invasively communicated to the implanted pacemaker, these commands having information contained therein that specifies the duration of selected time intervals associated with the operation of the pacemaker; and (2) means for graphically displaying a selected plurality of these time intervals in a visual representation that depicts when, within a predefined cycle, each displayed time interval begins and ends. In order to compare this prediction to actual performance, means are also provided in one embodiment for graphically displaying measured intercardiac ECG data, either real-time or stored, simultaneously with the display of the programmed time intervals, both displays sharing the same time-line axis.

The display means of the present invention further includes command-entering means for displaying various sets of command selections that can be made in programming or interrogating the pacemaker or analyzer-programmer system. Advantageously, such commands are entered, processed, displayed and executed in a concise, easy-to-understand, error-free manner. Further, th display means allows real-time data obtained from the implantable medical device, such as intercardiac ECG waveforms, to be graphically displayed in real time and/or stored for subsequent display and analysis.

BRIEF DESCRIPTION OF THE DRAWINGS

The above and other advantages and features of the present invention will be more apparent from the following more particular description thereof, presented in conjunction with the following drawings and appendices, wherein:

FIG. 2A is a simplified block diagram of the analyzer-programmer system-II (APS-II) of FIG. 1;

FIG. 3 is a block diagram of the telemetry head module of FIG. 2;

FIG. 6B is a timing diagram illustrating key waveforms associated with the operation of the ROM Pack of FIG. 6;

FIGS. 7A–7C are representations of some of the many types of displays generated by the APS-II on a touch sensitive screen, which displays allow an operator to select the displayed option by merely touching the appropriate area on the screen;

Figure 6A:
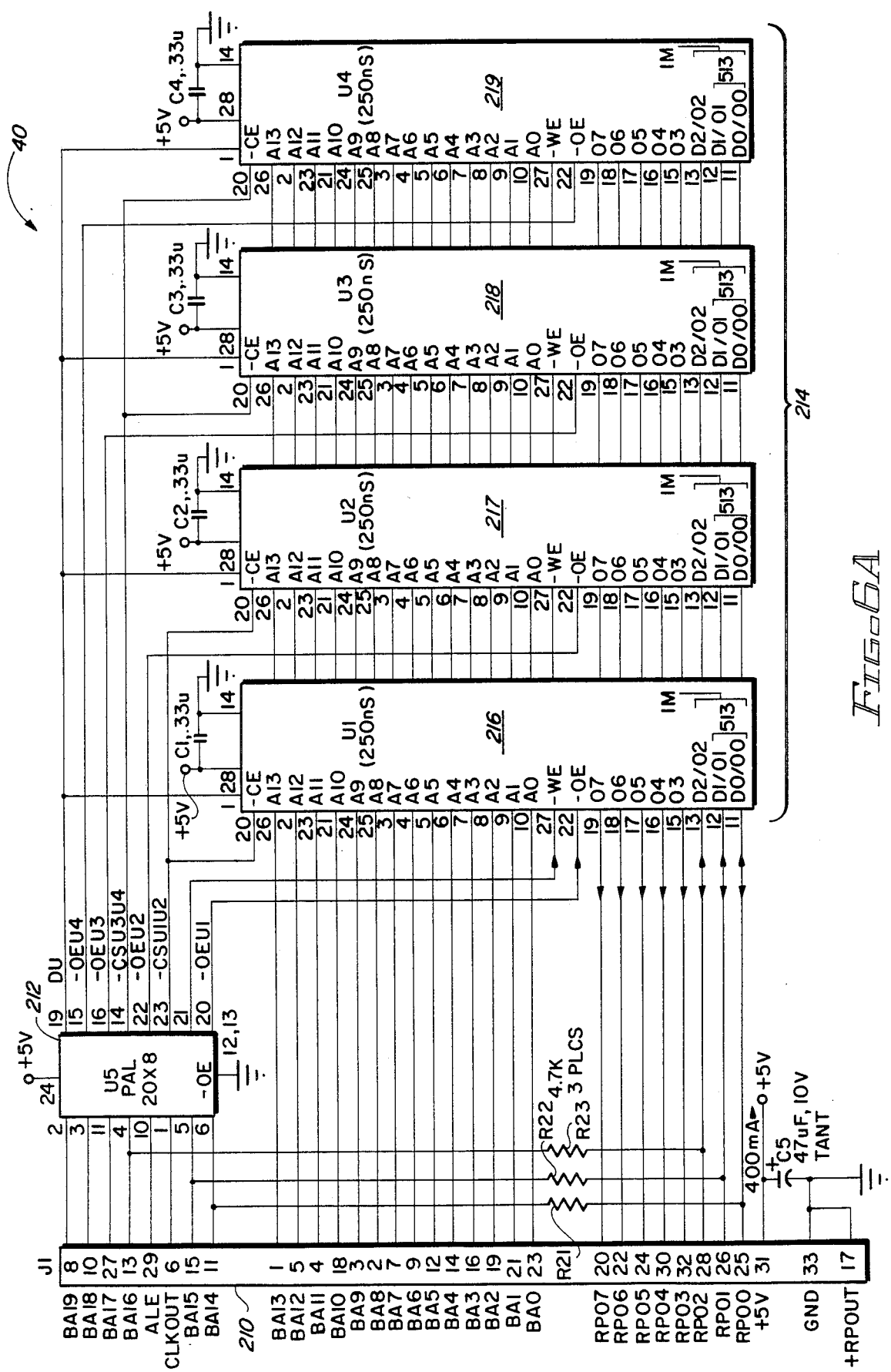
FIG. 6A is a schematic diagram of the Program Cartridge (ROM Pack) of FIG. 2.

Appendix A is the APS-II Product Specification;

Appendix B is a description of how an exemplary Programmed Logic Array (PAL) used within the ROM Pack of FIG. 6A is programmed; and Appendix C is a representative program listing of software used to control the interval programming features of the present invention.

DETAILED DESCRIPTION OF THE INVENTION

The following description is of the best presently contemplated mode of practicing the invention. This description is not to be taken in a limiting sense but is made merely for the purpose of describing the general principles of the invention. The scope of the invention should be ascertained with reference to the appended claims.

APS-II System Overview

The analyzer-programmer system of the present invention is incorporated into a programming device, hereafter referred to as APS-II, soon to be manufactured and sold by Pacesetter Systems, Inc., a Siemens Company, of Sylmar, Calif. As suggested by the device name, APS-II represents a second generation of the previously referenced APS, also manufactured and sold by Pacesetter Systems, Inc. APS-II includes improvements and enhancements not found in APS, while being more compact and less expensive than APS. APS-II provides a sophisticated, microprocessor-based programming system that can be used to noninvasively interrogate and program the programmable cardiac pulse generators (pacemakers) manufactured by Pacesetter Systems, Inc.

Some of the processing and display features of APS-II are described in previously-filed U.S. patent application Ser. No. 876,612, filed June 20, 1986, owned by a common assignee with this application. This previously-filed '612 application is incorporated herein by reference.

Figure 1:
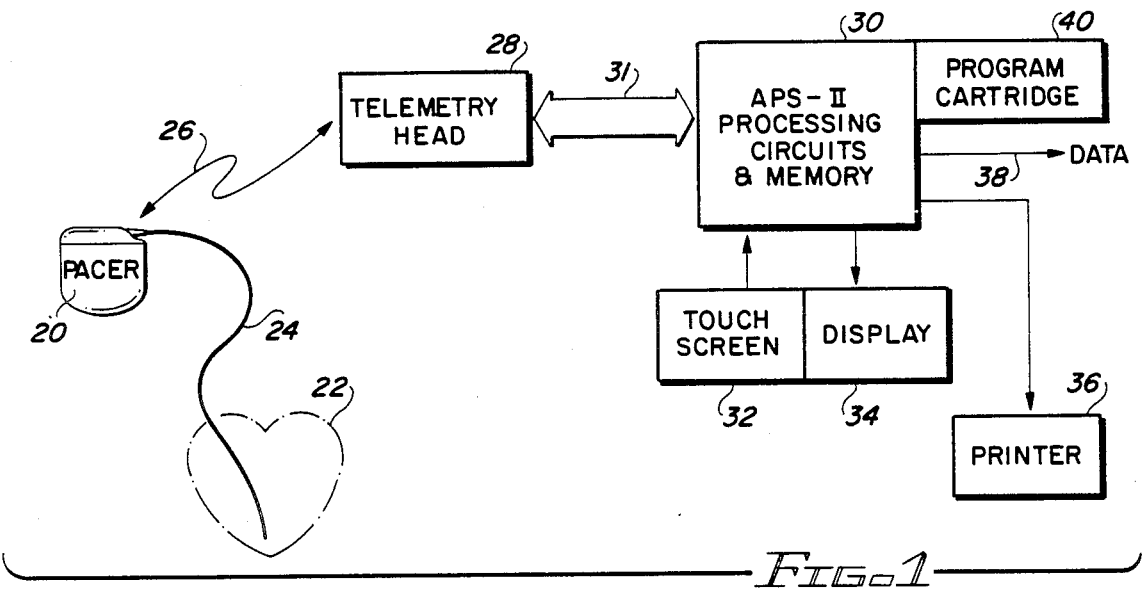
FIG. 1 is a system block diagram showing the main components of the present invention.

Turning now to FIG. 1, a very simplified block diagram of APS-II is presented. A programmable pacemaker 20, presumably implanted within living tissue, is in electrical contact with a heart 22 by way of at least one pacemaker lead 24. (It is noted that while the pacemaker 20 in FIG. 1 is presumed to be implanted, it need not be implanted for the APS-II to function. For example, for training purposes, it is quite common to use an APS-II with a non-implanted pacemaker that is connected to a heart simulator.)

The pacemaker 20 is typically a self-contained unit that is capable of both sensing natural cardiac activity and providing stimulating pulses to invoke paced cardiac activity. The operating characteristics of the pacemaker 20 can be noninvasively programmed by way of command signals received over telemetry link 26, which command signals are received from a telemetry head 28 connected to the APS-II processing circuits 30 by way of a connection cable 31. The command signals are generated within the APS-II processing circuits 30 as a function of operating commands received by way of touch sensitive screen 32. That is, as will be described in more detail below, an APS-II operator selects a desired command by touching a designated area on the touch screen 32, which designated area is defined by a particular pattern displayed on the display screen 34. Advantageously, the touch screen 32 overlays the display screen 34 so that all one need do to make a command selection is to touch the screen at the area indicated on the display for the desired command.

The pacemaker 20 is also capable of sending operating data and measured data over the telemetry link 26 to the telemetry head 28. The telemetry head 28 preliminarily processes this data and forwards it on to the APS-II processing and memory circuits 30. Data received at the APS-II circuits 30 may be displayed on the display screen 34, printed on a printer 36, and/or stored within the memory elements of the APS-II circuits 30 for subsequent retrieval and display. Alternatively or conjunctively, data received at the APS-II circuits 130 may be transmitted over an appropriate data channel 38 to a desired external device, such as a modem, an X-Y plotter, a tape or disk drive, or other peripheral device.

Operation of the APS-II processing and memory circuits is controlled by way of a program cartridge 40 that is detachably connected to the processing and memory circuits 30. Removable program cartridge 40 thus advantageously allows the operating characteristics of the APS-II device to be easily upgraded to include new features and to properly interface with new pacemakers, as new features and new pacemakers are developed. Such upgrading can occur at minimal cost because all that is required is a new program cartridge 40, rather than a whole new analyzer-programming system, as has been required in the past.

APS-II System Block Diagram

Referring next to FIG. 2A, a more detailed block diagram of the APS-II Processing Circuits and Memory 30 of FIG. 1 is shown. (It is noted that other elements from FIG. 1 are also shown in FIG. 2A, with like reference numerals being used to indicate like parts.) Essentially, the APS-II is made up of two major modules, the APS-II system unit and the Telemetry Head 28. Each of these major modules is further made up of many subassemblies and functional elements. The organization of the block diagram of FIG. 2A shows the major subassemblies and functional elements of the APS-II system unit. Many of these elements are conventional and no further description beyond that given below in connection with FIG. 2A will be presented herein.

Referring then to FIG. 2A, it is seen that at the heart of the APS-II is a microprocessor 42. In the preferred embodiment, microprocessor 42 is realized using a commercially available 80188 processor manufactured by Intel. As known to those skilled in the art, the 80188 processor is a highly integrated processor, containing several peripheral devices within its 68 pin package, such as a bus interface unit, a DMA unit, a programmable chip select unit, a timer unit, and an interrupt unit. It represents an advancement within the 8088 family of processors. It operates using an 8 MHz clock, which is derived from a 16 MHz crystal 60. A thorough description of the 80188 processor may be found in *Microsystem Components Handbook*, published by Intel Corporation (1986).

Coupled to the Interrupt Unit portion of the 80188 microprocessor 42 is a interrupt controller 62. Preferably, this controller 62 is realized with an eight input interrupt controller 8259A, also commercially available from Intel Corp. The inputs of the controller 62 are connected to high priority signals which are permitted to interrupt the processor tasks as required. These high priority signals may include (but are not limited to): latched parity error (LPE), indicating a single bit error occurred during a dynamic memory read operation; a keypress signal, indicating a continuous keypress was detected from the touchscreen electronics; an isolated input signal (EPL) received from the interface connector located at the rear of the APS-II; a surface ECG VCO signal, a periodic signal that facilitates a 16 bit timer value to be proportional to the period of the surface ECG interface VCO; or a vertical retrace interrupt request (VRTC) signal used to inform the 80188 processor of the availability of the video memory. The interrupt controller 62 interfaces with the microprocessor 42 and provides the microprocessor 42 with a binary code representing the source of selected interrupt signals. Priority levels are assigned by the software controlling the microprocessor 42 to enable the microprocessor 42 to respond appropriately to the interrupt signal having the highest priority level. A more definitive description of the 8259A may be found in the above-reference *Microsystems Components Handbook* (Intel, 1986).

The bus interface portion of the microprocessor 42 is connected to an address bus 64 and a data bus 66. A dynamic random access memory (DRAM) 68 is connected to both this address bus and data bus and provides 512K bytes of memory for use by the microprocessor 42 as it carries out its various functions. In the preferred embodiment, this 512K bytes of memory are provided in the form of eighteen 256K bit devices. Refresh and RAS/CAS timing of the memory 68 is provided by an integrated memory controller 70, realized with an Intel 8208 device.

Also connected to the address bus 64 and the data bus 66 is non-volatile memory 72. Memory 72 is preferably realized using a programmable read only memory (ROM) device which has been programmed to contain the power-up initialization software for the microprocessor 42 and the programs that are active when the program cartridge 40 is removed from the APS-II system unit 30.

Static random access memory (RAM) 72 is likewise connected to the address bus 64 and the data bus 66. In the preferred embodiment, this memory provides an additional 8K bytes of storage for operator selectable variables or additional software options. Advantageously, the data stored in static RAM 74 is maintained non-volatile by a replaceable battery 76.

The program cartridge 40 is an operator-replaceable program memory cartridge that is installed into the main printed wiring board at the rear of the APS-II housing 44 so as to also be connected to the address bus 64 and the data bus 66. The memory capacity is approximately 511K bytes when fully populated. In the preferred embodiment, program cartridge 40 is realized with ultraviolet-erasable programmable read only memory (UV-EROM) devices. The program cartridge 40 is described in more detail hereinafter in connection with the description of FIGS. 6A and 6B.

Further connected to the address bus 64 and the data bus 66 is a 64K display memory 43. Display circuits 45 and a cathode ray tube (CRT) 46 combine with the display memory 43 in order to provide the APS-II's display 34 (FIG. 1). The visible portion of the display is comprised of 480 by 240 bit-mapped pixels upon a 7 inch diagonal measure CRT 46. The video image to be displayed is written into the display memory 43 by the host microprocessor 42 through the use of direct memory access (DMA) and a number of programmable array logic (PAL) devices and medium scale integration (MSI) components. The data bus 66 and the address bus 64 are also used to transfer data into display memory 43. Once in display memory 43, the image is transferred to the appropriate pixels of the CRT 46 by means of conventional display circuits 45.

Still referring to FIG. 2A, power for the APS-II is provided by power supply 78. In the preferred embodiment, power supply 78 provides 150 Watts of power derived from an input power source of 110 VAC, 60 Hz. Output voltages are +5 volts, +12 volts, and +24 volts dc.

In order to unburden the host microprocessor 42 from the data being received from or sent to the various input/output (I/O) devices, another microprocessor 80 is connected as a slave microcomputer to the data bus 66. This slave microprocessor is realized in the preferred embodiment with an 8742A IO processor, available from Intel Corp. Essentially, the 8742A IO processor, using an UV-EROM 2K byte memory that operates at 11 Mhz, functions as an intelligent buffer in interfacing with the touchscreen 32, an annunciator 82, a real-time clock 84, and the printer 36. Further details associated with the 8742A processor may be found in the *Intel Microsystem Components Handbook*, Vol. II, p. 5-826 (Intel 1985).

The components interfacing with the slave microprocessor 80 will now be briefly described. Annunciator 82 is a speaker that is used to emit a tone for user feedback or a "click" when a keypad (the touchscreen 32) is touched. Touchscreen 32 is a touch-sensitive keypad that fits over the CRT display 46, thereby allowing the system to be entirely "menu-driven". The touchscreen returns the coordinates of the point on the screen that are depressed, which coordinates can be correlated and compared with the coordinates of menu selections that are displayed by the CRT, thereby providing an indication of which displayed keys have been selected. Real time clock 84 is used to keep track of the year, month, date, hour, minute, and second. Any of several commercially-available clock chips can be used for this purpose. A 32768 Hz crystal is used to provide frequency stability for the clock signal used to drive clock chip 84. Also, a battery 88 provides power to the clock chip 84 when the power supply 78 is turned off, thereby allowing clock 84 to maintain an accurate indication of the time and date. Printer 36 is a thermal printer that utilizes 416 elements, 102 elements per inch, and that prints at a speed of 1 inch per second. This speed allows real-time ECG printouts to be made, if desired.

Still referring to the block diagram of FIG. 2A, it is seen that data bus 66 is also tied into serial I/O controller 90, the function of which is to send and receive data via an RS-232 interface and/or other data interfaces, and to maintain communications with the telemetry head 28. Serial I/O controller 90 is realized using an 82530 Serial I/O Controller available from Intel Corp, or a Z8530 Serial I/O Controller available from Zilog Corporation. Further details associated with the operation and use of the serial controller 90 can be found in the *Zilog Z8030/8530 SCC Serial Communications Controller Technical Manual* (Zilog Corp. 1983).

An isolated functions module 92 is coupled to the serial I/O controller 90 via a serial I/O bus 94 and a parallel I/O bus 96. As shown in FIG. 2A, data may be sent to the isolated functions module 92 by way of the parallel bus 96. Data may also be sent or received from the isolated functions module 92 by way of bidirectional serial bus 94. Both buses interface with the isolated functions module 92 through opto-isolators 98. The isolated function module includes three sub-modules that must be isolated from the rest of the APS-II circuitry. These sub-modules are a surface ECG amplifier 101, an RS-232 communications interface 103, and an Electro-physiology (EP) interface 105. Isolated power for the isolated function module 92 is provided by DC/DC converter 107, realized with a Burr-Brown 722 DC/DC converter.

Figure 2B:
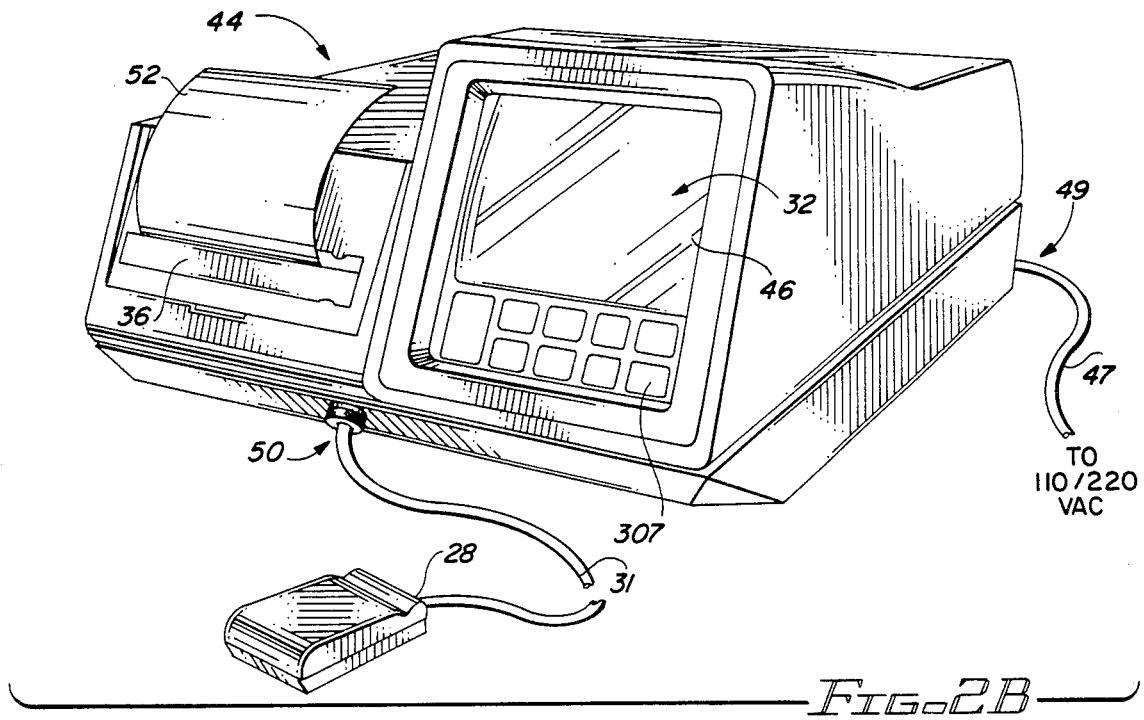
FIG. 2B is a perspective view of an APS-II device.

FIG. 2B illustrates a housing 44 within which the APS-II system unit components are housed. In accordance with one embodiment of APSII, all the circuits of FIG. 2A, with the exception of the telemetry head module 28, are housed within housing 44. In accordance with an additional embodiment of APSII, even the circuits of the telemetry head module 28, except for the coil assembly 117 (see FIG. 3), are housed within housing 44. As can be seen from FIG. 2B, the CRT screen 46, over which touchscreen 32 is laid, provides a readily visible and accessible means for viewing displays and selecting commands. Similarly, the printer 36 provides a paper copy 52 of that which is displayed on the screen of the CRT 46, or other desired information, as selected by the various commands available through touching the touchscreen. The telemetry head module 28 is attached to cable 31 which plugs into a connector 50 located on the bottom front side of the housing 44. A power cord 47 plugs into a socket 49 at the rear of the housing and allows the APS-II to be powered from any suitable electrical outlet providing 110/120 VAC, 60 Hz. The power cord 47 may be stored on the bottom of the housing 44 for ease of transportation and storage. Similarly, the telemetry head 28 (first embodiment), or telemetry coil assembly 117 (second embodiment), when detached, can be stored in a removable front cover (not shown) when not in use. The various connections associated with the Isolated Functions Module 92, discussed above in connection with FIG. 2A, are also made available through appropriate connectors located either along the bottom front or the rear of the APS-II housing 44.

Telemetry Head

Referring next to FIG. 3, a block diagram of the telemetry head 28 is shown. As mentioned, in a first embodiment, telemetry head 28 includes all of the components shown in FIG. 3, including a microprocessor 115. Thus, in this embodiment, telemetry head 28 may be considered as a "smart" telemetry head because it includes processing circuitry capable of performing many of the signal and telemetry processing functions needed to efficiently communicate with an implanted pacemaker independent of the APS-II system unit circuits contained within the housing 44 (FIG. 2B). In an alternative second embodiment, telemetry head 28 may include only a telemetry coil assembly 117, with the balance of the circuitry shown in FIG. 3 being included within the housing 44. In this second embodiment, telemetry head 28 would be considered a "dumb" telemetry head because it would be totally dependent upon the APS-II system unit circuits for its operation. In either embodiment, because telemetry head 28 is attached to the APS-II system unit by way of detachable cable 31 (FIG. 2B), the telemetry head 28 is effectively a field-replaceable module that exists as a peripheral to the APS-II system unit.

Before describing the circuits of the telemetry head 28, it will be helpful to present a brief overview of the telemetry head's external and internal construction. In the first embodiment, telemetry head 28 is housed within a two-piece ABS plastic package, best shown in FIG. 2B. The package is assembled with four screws, facilitating factory service of the internal electronics. The package is not sealed against moisture and as such should not be directly exposed to solvents. The indicator light emitting diode (LED) 113 (FIG. 3) is positioned within the housing so as to be visible on the upper (inactive surface) of the module.

Internally, the telemetry head 28, according to the first embodiment, is made up of an electronic assembly that consists of a printed wiring board (PWB) and a telemetry coil assembly 117 installed onto a ferrite form. The PWB is multi-layer glass reinforced plastic design with a shield layer on the component side, facing the ferrite assembly. The PWB is installed with the component side and shield layer facing the coil and ferrite assembly to maximize the separation between the coil assembly and the PWB. This is done to minimize the "loading" effect upon the telemetry coil imposed by the PWB and to minimize the coupling of noise from the PWB circuits into the coil.

The PWB components consist of sensitive signal detection and filtering circuits, amplifiers, signal conversion circuits, and a microcontroller. These circuits will now be briefly described with reference to the block diagram of FIG. 3. While the discussion that follows is directed to the first embodiment of a "smart" telemetry head, it is to be understood that the circuit descriptions apply equally well to the second embodiment where the circuits are housed within the main APSII housing 44.

Power for the telemetry head 28 is provided by the host APSII power supply 78 (FIG. 2). However, this power is further regulated with regulator 119 (FIG. 3). In the embodiment shown, the input power to regulator 119 is +24 volts and +9 volts, and the output regulated power provided by regulator 119 comprises +12 volts, +9 volts, +18 volts, and two independent lines of +5 volts. Regulator 119 is realized using commercially available regulator circuits, such as the LM324, LM7818, and LM7805, available from Texas Instruments.

At the heart of the telemetry head circuits is a microprocessor 115. In the embodiment shown, microprocessor 115 is realized using a commercially-available single chip 8-bit 8751 Microcontroller, available from Intel. The 8751 operates using a 12 Mhz clock generated by an external crystal 114. Advantageously, the 8751 is preprogrammed and thus dedicated to control the telemetry module hardware. Full-duplex, high speed, serial communication is provided with the microprocessor 115 over TX and RX data lines 121 and 123, respectively, by virtue of an integral Universal Asynchronous Receiver Transmitter (UART) that is included within the 8751 chip. Buffering is provided by high-speed CMOS inverter gates 124 and 125. Data lines 121 and 123 thus comprise the high speed serial communication link 31 shown in FIG. 2A.

The embodiment shown in FIG. 3 includes separate coils 116 and 118, wound on the same ferrite core (but with different orientations) to enable communications between the telemetry head and two different families of pacemakers. Each coil 116 or 118 has a telemetry oscillator associated therewith, identified in FIG. 3 as block "TLM OSCILLATORS" 127. Signals are transmitted from the appropriate coil 116 or 118 (referred to as uplinking) by modulating the respective oscillators 127 with an appropriate data signal. This data signal is generated by the microprocessor 115 and sent to the telemetry oscillator 127 over signal line 129. In the preferred embodiment, a Manchestor data format is used. The oscillator supply voltage is set and maintained, by servo circuits 133, to a desired level, such as +9 volts, by a control signal provided on signal line 131, in order to control the uplinking capabilities (e.g.-,range) of the transmitted signal.

Downlinking, or the receiving of signals from an implanted pacemaker, is accomplished in the following manner. Conventional receiving circuits 135 and 137 sense and amplify any signals received through coils 116 and 118 of the coil assembly 117. Modulation detection is then performed using amplitude (AM) detector 139. Advantageously, a self-test calibration modulator 141 is provided to simulate a typical pulse generator modulation for the purpose of test and calibration. This feature provides assurance of the telemetry accuracy by measurement of the frequency-to-voltage transfer function, discussed below, and facilitating the creation of a calibration factor. Either the output from the calibration modulator 141 or the output of the AM Detector 139 may be selected for presentation to amplifier 143 by switch circuitry 145, which switch circuitry is controlled by the processor 115.

The output signal from amplifier 143 is directed to low pass filter 147. Amplifier 143 and filter 147 serve to buffer, amplify and condition the signal prior to digitization. Digitization of the signal is accomplished by first presenting the signal to zero-crossing detector 149 in order to convert the analog information of the signal to a digital representation of frequency. This frequency information signal is then applied to three functional sections: (1) the processor 115, which processor measures the frequency directly (such frequency measurement is essential for Manchester demodulation); (2) a missing pulse detector 151 (whereat a low frequency triggers an output signal from the detector 151 that signals the presence of a marker in the analog downlink, thereby significantly unburdening the processor 115; and (3) a frequency-to-voltage converter 153, formed by a one-shot circuit 155 and a 100 Hz low-pass filter 157.

The output signal from the frequency-to-voltage converter 153, the output signal from the calibration modulator 141, and an output signal from an absolute-value detector 159 (connected to the input of the zero-crossing detector 149) are all directed to a multiplexer 161. Multiplexer 161, which is controlled by the processor 115, selects one of these three input signals for presentation to A-to-D converter 163. A sample and hold circuit 162 comprises the front end of the A-to-D converter 163. In the preferred embodiment, A-to-D converter 163 provides a serial-interfaced digital output signal having an 8-bit resolution over the range of 800 Hz to 2500 Hz. This serial digital signal is presented to the processor 115, where it is processed as required and eventually passed on to the serial communications line 121 for presentation to the APS-II unit 30 (FIG. 2A).

The telemetry head module 28 also includes a DC/DC Converter 165 for generating the negative 16 volt supply voltage used by the telemetry oscillators 127. This converter 165 is enabled only during uplinking (transmission of signals to the pacemaker), as it is only then that the telemetry oscillators are operational.

Figure 4:
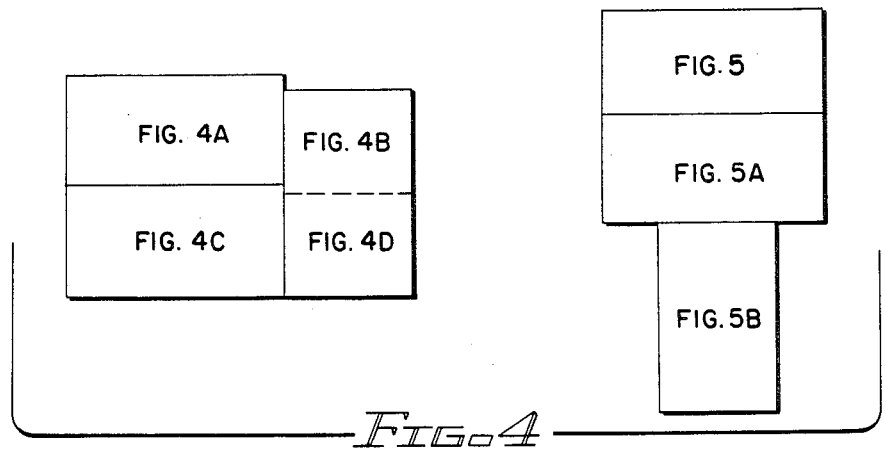
FIGS. 4A–4D are schematic diagrams of the telemetry head module circuits of FIG. 3, with FIG. 4 being a map diagram showing the interrelationship between the respective schematic diagrams of FIGS. 4A–4D.

Referring next to FIG. 4, and FIGS. 4A-4D, the schematic diagram of the telemetry head module 28 is shown. FIG. 4 is a map diagram that illustrates how the four schematic diagrams, FIGS. 4A-4D, interrelate one with another. It is noted that the same reference numerals used in FIG. 3 are used to indicate like parts of the schematic diagrams of FIGS. 4A-4D. A detailed explanation of the operation of the circuits shown in the schematic diagrams of FIGS. 4A-4D is not provided, as such will be self-evident to those skilled in the art. However, a brief explanation of which circuits are included in which figures will be presented to aid in understanding the interrelationship between the various circuits.

In FIG. 4A, the coil assembly 117, comprising the two separate coils 116 and 118, is shown connected to telemetry oscillators 127, which are realized with transistors Q1 and Q2. The output of these coils 116 and 118 is also directed through diodes CR3 and CR4 to AM Detector 139, realized with an RC network comprised of capacitor C14 and resistors R11 and R14. Two shunt switches, not shown in the block diagram of FIG. 3, are coupled to the output signal lines of coils 118 and 116, respectively, so that the appropriate signal line can be shunted to ground when not in use. These shunt switches are realized with FET transistors Q4 and Q5. A quad control relay U3 provides four independent mechanical switches that are used to selectively turn on the shunt switches Q4 and Q5, or the telemetry oscillators Q2 and Q3. Control of the quad switch U3 is obtained from signal lines A1 and A2, which originate at the microprocessor 115, shown in FIG. 4C The high speed serial communication lines 121 and 123 are also shown in FIG. 4A as being connected to pins 3 and 4 of cable connector TB2. Cable connector TB2 corresponds to the telemetry head connector 50 shown in FIGS. 2A and 2B. Pins 1 and 2 of connector TB2 carry +24 and +9 volts respectively to the voltage regulator 119.

Figure 4B:
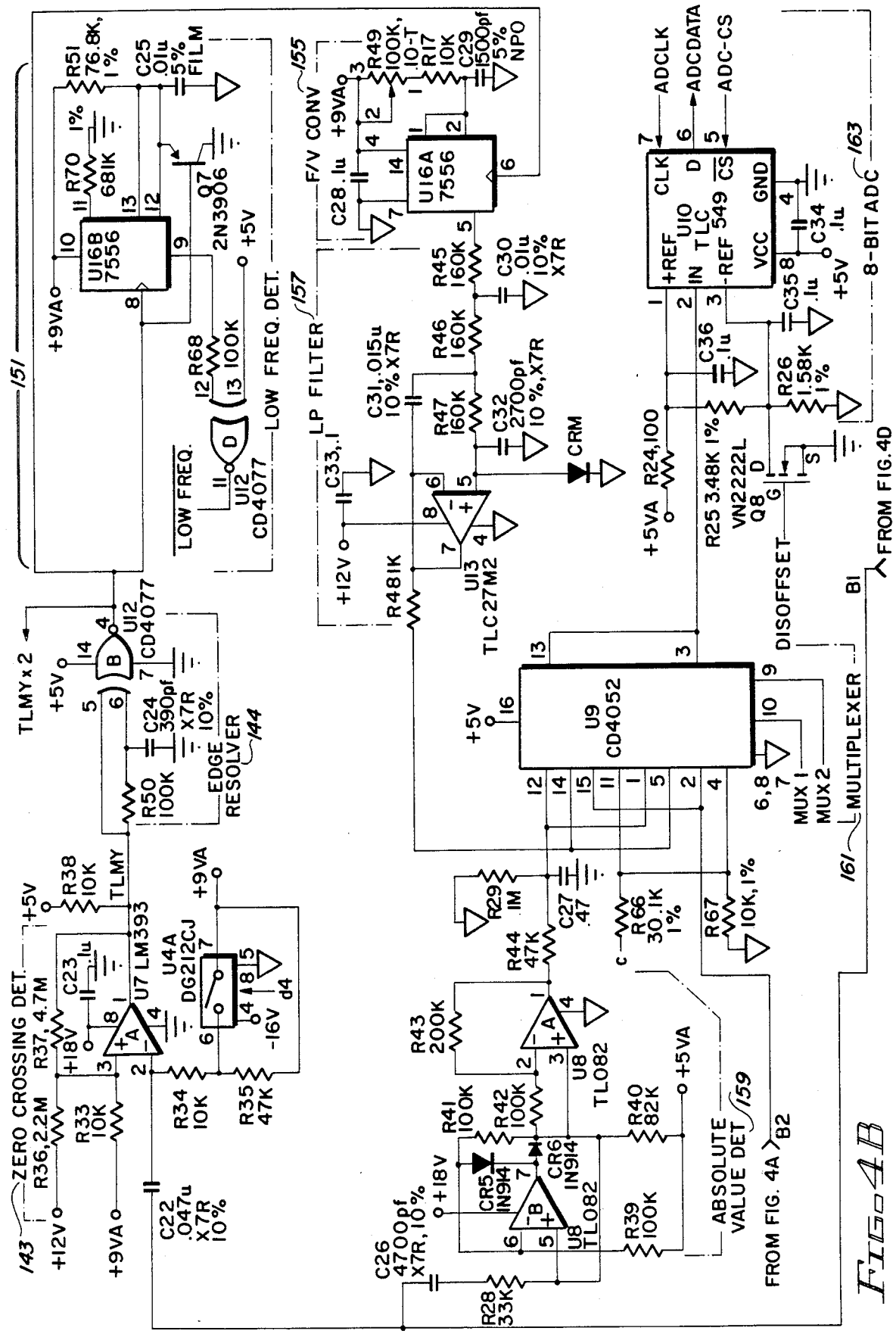
Figures 4C, 4D:
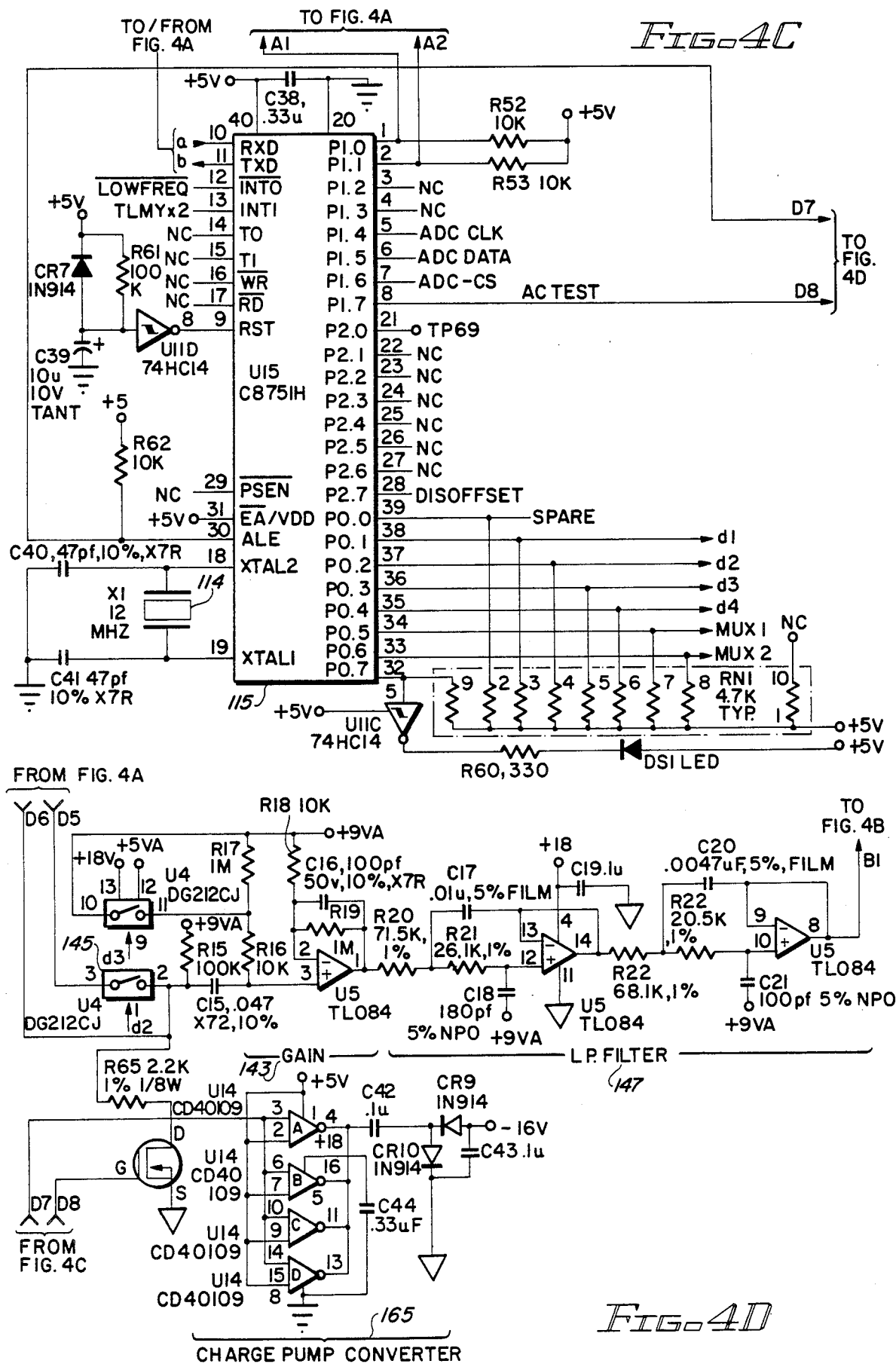

Referring next to FIG. 4D, the output signal from the AM Detector 139 (FIG. 4A) is next serially connected to switch 145, amplifier 143 and low pass filter 147, the schematic diagrams of which are all shown in FIG. 4D. Amplifier 143 is realized with one of the operational amplifiers included in integrated circuit U5, while low pass filter 147 is realized using two additional operational amplifiers also included in U5. Further shown in FIG. 4D is the DC/DC converter 165, also referred to as the Charge Pump Converter, which circuit generates a negative 16 volts by pumping up a capacitor C42 with a negative charge at a 2 MHz rate, the 2 Mhz pumping signal being obtained over signal line D7, which originates at the "ALE" terminal of the microprocessor 115 of FIG. 4C.

Referring next to FIG. 4B, it is seen that the output signal from the Low Pass Filter 147 (FIG. 4D) is directed to the zero-crossing detector 143 and to the absolute value detector 159, both circuits of which are realized in conventional manner. An edge resolving circuit 144 supplements the performance of the zero-crossing detector 143 in order to clearly define signal transitions. In effect, this edge resolving circuit doubles the demodulated telemetry frequency.

Sill referring to FIG. 4B, a Low Frequency Detector 151, referred to as the Missing Pulse Detector in FIG. 3, monitors the frequency of the output signal obtained from the edge resolving circuit 144 and provides a "low frequency" trigger signal to the microprocessor 115 whenever a 630 Hz marker signal is sensed within the demodulated telemetry signal. The output of the resolving circuit 144 is also connected to the frequency-to-voltage converter circuit 153, realized using one shot circuit 155 followed by low pass circuit 157. The outputs of the frequency-to-voltage circuit 153, the absolute value detector 159, and the calibrated test pulse (obtained from the emitter of transistor Q1 in FIG. 4A), are all tied into multiplexer 161, realized with integrated circuit U9 in FIG. 4B. One of these inputs is selected by the multiplexer 161 and delivered to the 8 bit A-to-D converter 163. The serial digital output of the A-to-D converter 163 is presented to the microprocessor 115, shown in FIG. 4C, over the signal line identified as ADCDATA.

APS-II

Figure 5:
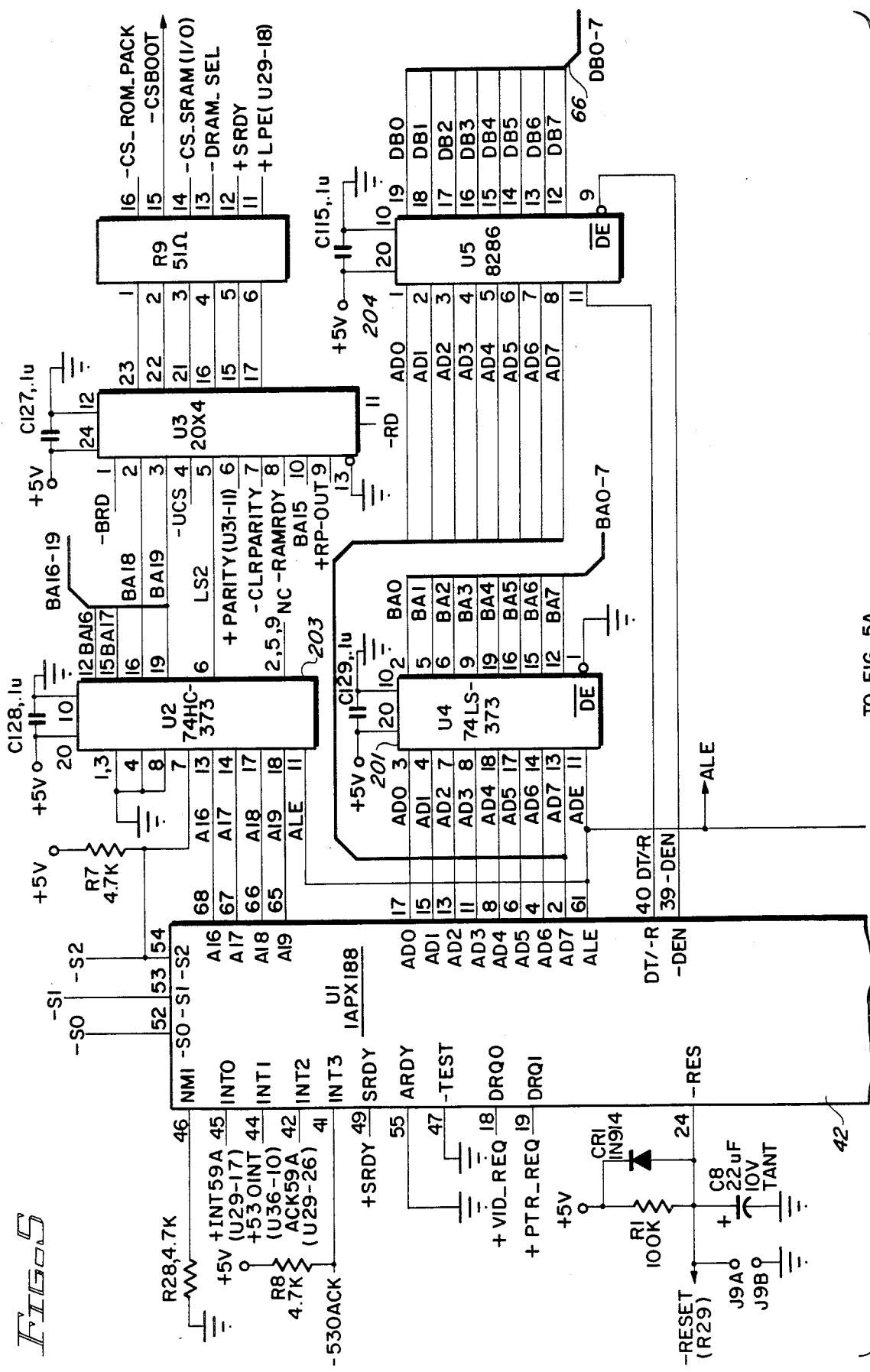
FIGS. 5A and 5B are schematic diagrams of key portions of the APS-II shown in FIG. 2.
Figure 5A:
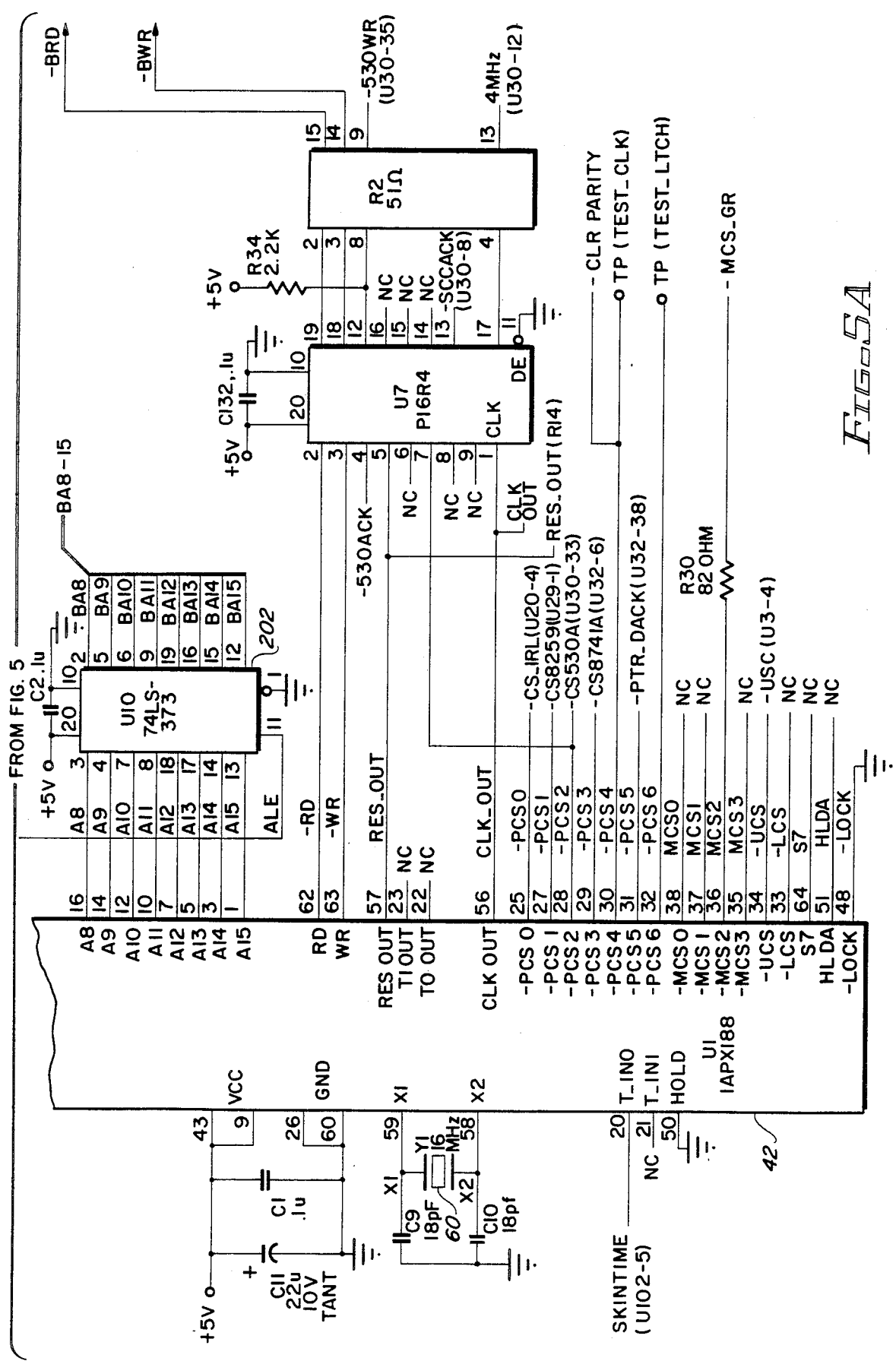

Referring next to FIGS. 5A and 5B, a schematic diagram of key portions of the APS-II circuits is shown. Like numerals are used to describe the elements of FIGS. 5A and 5B and FIG. 2. It is noted that not all of the APS-II circuits are included in FIGS. 5A and 5B because not all are relevant to the present invention. Further, it is submitted that, for those skilled in the microprocessor art, a block diagram, such as is shown in FIG. 2, accompanied by a brief description of each of the blocks or circuit functions within the block diagram, as has been provided above, is sufficient to enable such skilled person to practice the invention. For those unskilled in the art, who desire to know additional details associated with the operation and design of the APS-II device, reference is made to Appendix A, filed concurrently herewith, wherein is found the "APS-II Product Specification."

Referring then to FIG. 5A, the main microprocessor 42 is shown, including all the various connections that are made to its input/output pins. (The processor 42 is also identified in FIG. 5A as U1.) Of relevance to the present invention is the manner in which the data bus 66 and the address bus 64 interconnect the processor 42 with the Program Cartridge 40 (FIG. 2). The pins labeled AD0–AD7, A8–A15, and A16–A19 on the processor 42 comprise the data terminals through which appropriate data words may be received from or sent to the processor. When data is being sent from the processor 42, these data terminals are connected to data latches 201, 202, and 203. The output terminals of data latch 201 are identified as BA0–BA7, and correspond to processor data lines AD0–AD7. Similarly, the output terminals of data latch 202 are identified as BA8–BA15 and correspond to processor data lines A8–A15; and the output terminal of data latch 203 are identified as BA1-6–BA19 and correspond to processor data line A1-6–A19. Any or all of these data lines, BA0–BA19, can thus be used to transfer data from the processor 42 to a desired location.

When data is being received by the processor 42, data is received on data terminals AD0–AD7 from octal bus transceiver 204, which transceiver, in turn, receives the data over signal lines identified as DB0–DB7. Whether the particular data on signal lines BA0–BA19 and DB0–DB7 comprises data or a data address depends upon the source or destination of the data and how the source or destination is configured. Typically, signal lines DB0–DB7 are used to transfer 8-bit data words from or to the processor 42, and these signal lines thus function as the data bus 66 (referenced in FIG. 2). Similarly, signal lines BA14–BA19 typically are used to transfer a 6-bit data address from the processor, which address indicates a specific location within a designated device to or from which the data is to be sent or received. Thus, these signal lines BA14–BA19 may be thought of as the address bus 64 (referenced in FIG. 2), although it is to be understood that other signal lines, such as BA8–BA13, may also be used (and are used) to supplement the address information contained in bits BA14–BA19.

With reference now to FIG. 5B, it is seen that signal lines BA0–BA19 (comprising the address bus 64) are connected directly to a Rom Pack Connector 206. Similarly, signal lines DB0–DB7 (comprising the data bus 66) is connected to the Rom Pack Connector 206 via octal bus transceiver 208. (As is known to those skilled in the art, a bus transceiver device is a two-directional device that allows data, upon receipt of a first set of proper control signals, to pass through the device in one direction; and, upon receipt of a second set of proper control signals, allows data to pass through the device in the opposite direction.) The Program Cartridge 40 (FIG. 2) plugs into the Rom Pack Connector 206.

Program Cartridge (Rom Pack)

Referring next to FIG. 6A, a schematic diagram of the Program Cartridge 40 is shown. This cartridge 40 includes an address decoder 212 and memory 214. A connector 210, configured to plug into the Rom Pack Connector 206, connects the address bus data BA1-4–BA19 to the decoder 212. Other address data lines, BA0–BA13, are connected directly to the memory 214. Data bus lines, identified in FIG. 6A as RP00–RP07 (corresponding to DB0–DB7, respectively, of FIG. 5) are likewise connected to the memory 214 by the connector 210. Memory 214 is realized, for the embodiment shown in FIG. 6A, using four commercially available memory devices, 216–219. These devices each vary in size from 32K bytes to 128K bytes, thereby providing up to a total of 512K bytes of addressable memory space. Advantageously, each of the memory devices 216–219 are installed into the cartridge 40 using sockets, thereby allowing a variety of pin compatible EROM devices, for example, to be inserted into the cartridge. By way of illustration, commercially available EROM devices ranging from the 27256 and 27512, to the more exotic 27513 or the 27011, available from Intel or other semiconductor manufacturers, may be used as the memory devices 216–219.

The decoder 212 is realized with a programmed logic array (PAL). In the preferred embodiment, the PAL 212 is replaceable, as are the memory devices 216–129. Using a replaceable PAL allows the PAL to be replaced if a memory upgrade is required Further, the use of a replaceable PAL advantageously permits the use of different types of memory devices 216–219 to be used within a single memory array 214. Further details associated with the design of the PAL 212 for a preferred embodiment of the present invention are provided in Appendix B.

The PAL 212 provides the interface between the desired type of memory device and the processor's address/data/control busses. It is a function of the PAL 212 to make addressing and data signaling differences (due to the use of different types of memory devices) invisible to the processor 42, thereby minimizing any problems or concerns associated with considering which memory devices are present. Thus, advantageously, no special concessions for memory interface, except for size, need to be made. The processor 42 need only present an address instruction on the address bus, which instruction is then latched; issue a read signal; and then retrieve the data from the memory 214.

Thus, PAL 212 serves as the controller for the memory devices 216–219. That is, the PAL decodes address commands and generates appropriate select/control signals for retrieving the desired data from the decoded address, including generating signals required to effectuate the bank switching method described below. In the preferred embodiment, PAL 212 is realized using a commercially available logic array 22V10 available from Advanced Micro Devices. This array is programmed as set forth in Appendix B. The equipment used to program the 22V10 is well known in the art, and is readily available from numerous sources, such as Advanced Micro Devices (AMD). In practice, it is common in the art for manufacturers of logic array devices, such as AMD, to program the device for a customer according to the customer's specifications, such as those set forth in Appendix B.

Referring momentarily to FIG. 6B, a simplified timing diagram is shown that functionally illustrates the above operation. At some point in time, the ALE signal changes states, indicating that an address has been latched at which data is to be retrieved. According to conventional practices, it takes several clock cycles after the ALE signal changes states before the desired data can be retrieved and placed on the data bus, as shown for example by the typical bus access cycle defined in FIG. 6B. This is because there are typically several steps associated with fetching data from a given memory location, each step of which occurs sequentially as controlled by the basic clock (CLK) signal. In accordance with one embodiment of the present invention (wherein the 27513 or 27011 devices are used as the memory devices 214 of FIG. 6A), however, a novel bank switching method of addressing is used that advantageously allows data to be fetched on the next rising edge of the system clock after the ALE signal changes states, i.e., within the same basic clock cycle. This method is made possible by a configuration wherein the address bus is coupled to the data bus through resistors, thereby allowing the address information to go onto the data bus during the input mode of the data bus. Thus, when the PAL strobes the write pulse to the memory devices 114, the desired bank of memory devices is automatically selected. In FIG. 6A, this configuration is shown by the address bus signal lines BA14–BA16 being coupled to the data bus signal lines RP00–RP02, respectively.

It is noted that the bank switching method and configuration described above goes against the conventional teachings concerning the use and operation of the commercially available memory devices, such as the 27513 device, manufactured by Intel Corporation. For example, in the *Memory Components Handbook* (Intel 1986), in the description of the 27513 device, which begins on page 4-90, there is a warning given (on page 4-96) that "[c] are should be taken in organizing software programs such that the number of page changes is minimized." The clear intent of the manufacturer of the device is thus to first select a page and then make subsequent accesses within that page (i.e., perform a multiple-step operation that requires several clock cycles). In contrast, the present invention does not use the 27513 device in that manner. Rather, in accordance with the present invention, the PAL 212 is designed so as to rapidly and dynamically change pages in a way that is transparent to the processor 42 (FIG. 5A). Hence, no page-select-write operation is performed as recommended by the teachings of the art. Thus, to the processor 42, the memory device 214 appears as a linearly addressed part that does not require a separate page-select write operation in order to access desired pages thereof. The result is a shorter access time and a significant reduction in the amount of overhead software that is required to retrieve data from the program cartridge 40 (FIGS. 2 and 6A).

APS-II Displays

As has been previously described, the APS-II uses the combination of a conventional display 34 over which a touch-sensitive screen 32 is placed (see FIGS. 1 and 2A and accompanying text) in order to provide a means for operator-selected commands and controls. Such a combination advantageously eliminates the need for the more conventional, and sometimes threatening (especially in a medical environment), keyboard that so commonly is used to input commands to a computer-type system. Further, the combination allows for a wide variety of clear, precise, understandable instructions to be given to an operator in a way that makes it difficult for the operator to make a command-entry mistake. These and other advantages of the touch-sensitive screen and display combination are explained more fully in the APS-II Technical Manual, submitted herewith as Appendix A. Only a brief description of some of these displays is presented here to provide a basic understanding of the manner in which the displays are generated and commands entered.

The manner of electronically generating a display on a CRT 46 (FIG. 2), or other display device (such as an LED screen) is conventional, and those skilled in the art can readily repeat the same. Essentially, each display may be considered as a matrix of pixels organized into rows and columns. Any desired image can be created by simply causing appropriate pixels to assume a desired characteristic (dark, light, having a selected color, etc.). The image is stored within the memory circuits of the APS-II as a set of digital data words, each word defining the characteristics of a specific pixel or group of pixels. Hence, a desired image is displayed by simply retrieving the data words that define that image, and presenting those data words to the display circuits 45 (FIG. 2) of the display device, which display circuits decode and convert the data words into analog signals that generate the actual image on the display device.

All of the above is, as indicated, conventional and well known to those skilled in the art, especially to those skilled in the computer art. Further, it is known in the art to generate an image display, and to overlay that display with another display, thereby creating the appearance of having a first image in the background of the display and a second image in the foreground of the display. Any desired number of "tiers" (background, midground, foreground, etc.) of such image displays can be readily created.

With the above background of image display generation in mind, reference is now made to FIG. 7A where there is shown a representative display of the initial image display generated by the APS-II when it is first turned on. The display advantageously includes a specific instruction, shown generally at 300, that indicates what must be done by the operator in order to begin using the APS-II. This instruction, "PRESS HERE TO BEGIN", followed by a picture of a hand with a finger pointing to the area of the screen to be touched, leaves little room for misinterpretation. The area 302 to be touched is identified on the display as "Interrogate", and comprises a rectangular area defined by a shadowed border. Within this area, the display includes the image of a pacemaker 304 and a signal 306, signifying that during the interrogation process, information signals will be received from the pacemaker for the purpose of at least identifying the pacemaker.

As an alternative to touching the display screen at the interrogation area 302, as instructed by the image shown in FIG. 7A, the operator can also select "SYSTEM OPTIONS", as is also indicated in the instructions that are displayed. SYSTEM OPTIONS is selected by touching the designated permanent "Systems Options" area 307 below the main display (screen) area 46 (FIG. 2B). Other commands, in addition to SYSTEM OPTIONS, that are available for selection in the permanent display area are as shown in FIG. 7B.

In the event that SYSTEM OPTIONS are selected by touching area 307, a system options display 310 appears in the foreground of the display 46 as shown in FIG. 7C. As indicated in FIG. 7C, the background of the image being displayed remains the same as that shown in FIG. 7A. The foreground, however, comprises a defined area that has a border resembling a file or index card, with an index tab 312 along the top side thereof being labeled "System Options". Included within the System Options foreground display are six areas, each labeled with an appropriate title. Many of the titles are supplemented with a small picture or display symbol that further identifies the option that is available.

Figure 8A:
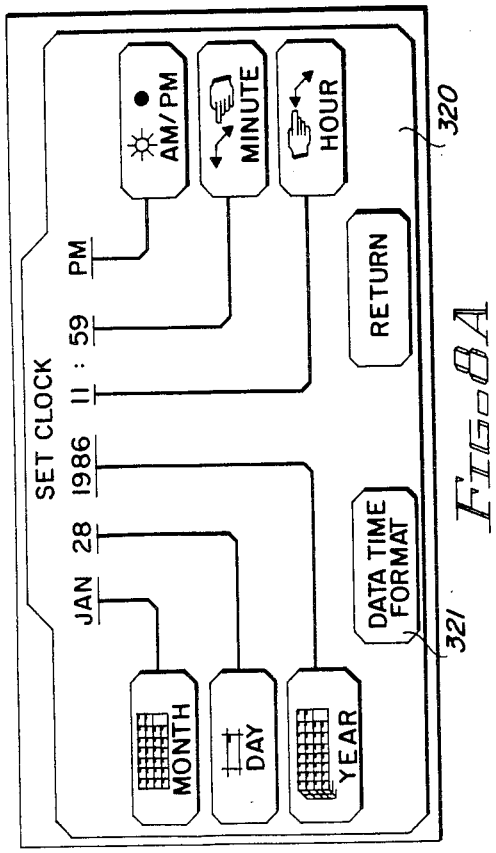
FIGS. 8A and 8B are representative displays generated by the APS-II used to set the clock within the APS-II.
Figure 8B:
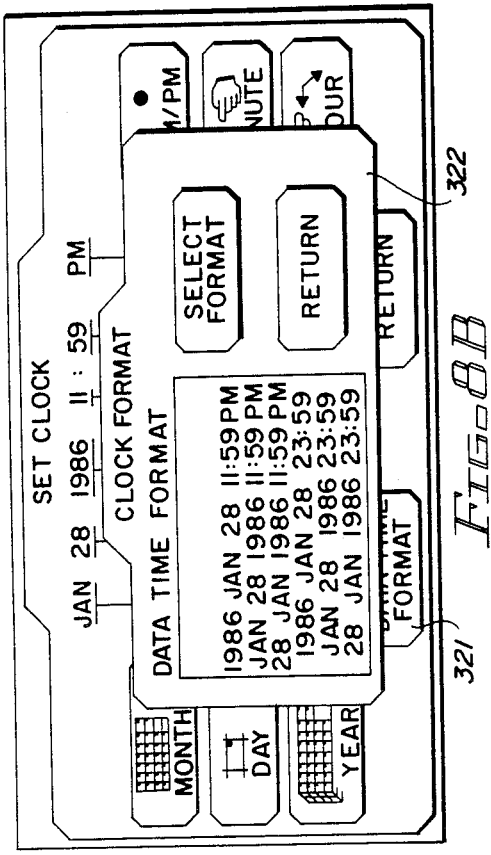

For example, still referring to FIG. 7C, one of the system option areas appearing in the system options display 310 is a "Set Clock" display 318. By touching this area 318, the operator initiates the Set Clock mode of the APS-II device. FIGS. 8A and 8B depict a "Set Clock" display 320 and a "Clock Format" display 322, respectively, that are used in conjunction with the Set Clock mode. That is, the Set Clock display 320 of FIG. 8A is displayed on the screen 46 when the Set Clock area 318 of the System Options foreground display 310 (FIG. 7C) is selected. In turn, when the Format area 321 of the Set Clock display 320 (FIG. 8A) is selected, then the Clock Format display 322 appears as a foreground display over the Set Clock display 320, as shown in FIG. 8B.

Figure 9A:
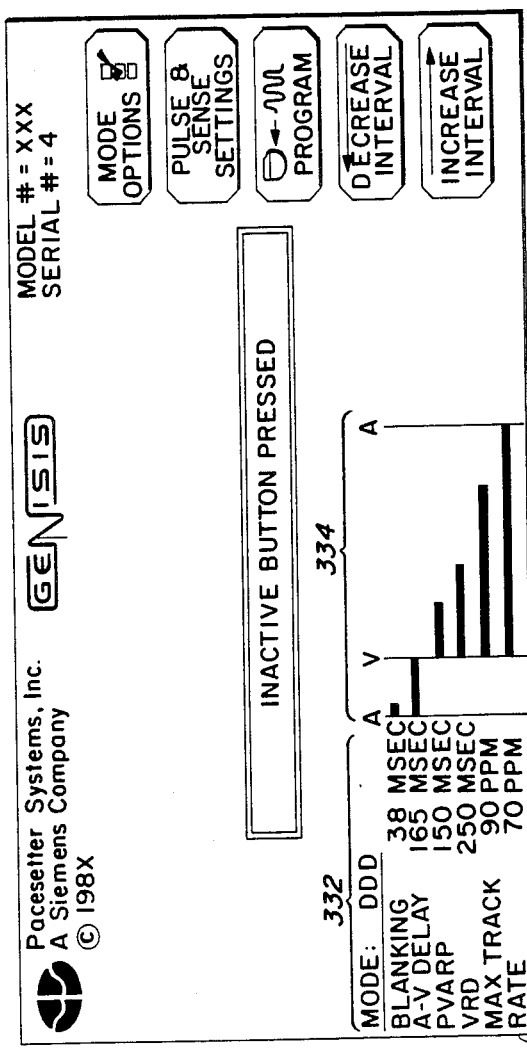
FIGS. 9A and 9B are representative displays generated by the APS-II used in connection with the interval programming features of the invention, with FIG. 9A showing a typical programmed interval display, and FIG. 9B showing a portion of a simultaneous ECG and interval programming display.
Figure 9B:
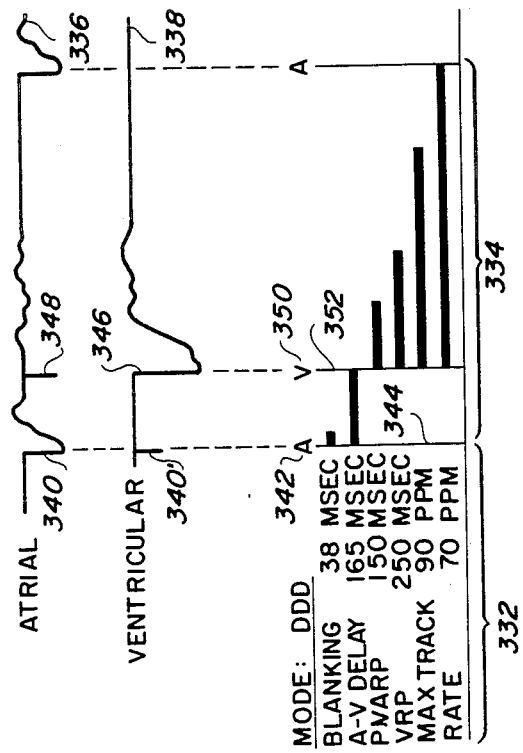

Referring next to FIGS. 9A and 9B, representative displays generated by the APS-II during interval programming are shown. FIG. 9A depicts a typical programmed interval display 330. Advantageously, this display 330 may include both a tabular display 332 of the programmed intervals associated with the particular pacemaker being interrogated, and also a time-bar display 334 of these same intervals. Both the tabular display 332 and the time-bar display 334, are generated and displayed in conventional manner, as previously described. However, as explained more fully below, it is the length of the various bars included within the time-bar display 334 that forms an important feature of the present invention.

The time bar display 334 comprises a scaled time display of the various time intervals. Thus, the blanking interval, which is shown in the tabular portion 332 of FIG. 9A as being 38 msec, is depicted in the time bar-display portion 334 of FIG. 9A as a horizontal bar having a length that is, on an appropriate horizontal time scale, proportional to 38 msec. As can be seen, this length is roughly 25% of the length of the A-V bar display, the corresponding programmed A-V interval having a value of 165 msec. (38 msec is 23% of 165 msec.) In other words, the time-bar portion 334 of FIG. 9A depicts the various programmed intervals as respective horizontal bars having lengths that are proportional to their respective times. Advantageously, each time bar begins at the horizontal location on the display that corresponds to the time (using the appropriate horizontal time scale) when the time interval begins within the programmed pacemaker. Thus, the time-bar display 334 presents the equivalent of a timing diagram of the indicated programmed intervals used within the pacemaker circuits. Such time diagrams have long been used by those skilled in the art in the form of charts, overhead projections, and the like, to illustrate the concept of how the various time intervals of an implanted pacemaker inter-relate one to the other. However, to Applicants' knowledge, electronically generated timing diagrams of a particular implanted or implantable pacemaker (showing the current programmed values) have never previously been incorporated into a display generated by a programming device in communication with the implanted (or implantable) pacemaker. Such a display advantageously allows a programmer of the pacemaker to visually see how the changing of one programmed time interval relates to and/or affects the other time intervals of the pacemaker.

Referring to FIG. 9B, another aspect of the display features of the interval programming technique of the present invention is illustrated. In accordance with the embodiment shown in FIG. 9B, the time interval display not only includes the tabular portion 332 and time bar display portion 334, as in FIG. 9A, but FIG. 9B also includes at least one intercardiac ECG channel that is displayed in synchrony with the time bar display.

In FIG. 9B, both an atrial channel intercardiac ECG trace 336 is shown, as is a ventricular intercardiac ECG trace 338. Both traces are displayed so as to be synchronized with the various time intervals displayed on the time bar portion 334 of the display. Thus, it is seen that the generation of an A-pulse 340 on the atrial channel display 336 appears as a large negative-going waveform, as is recognized in the art. A far-field small pulse 340' also may appear on the ventricular channel 338 as a result of the delivery of the atrial pulse by the pacemaker. The delivery of the atrial pulse causes the "A" marker 342 to be generated on the time bar portion 334 of the display of FIG. 9B, as has been done in the past. See, e.g., U.S. Pat. No. 4,596,255. However, unlike the past, a long vertical bar 344 is generated with the "A" marker that indicates the beginning of the blanking interval and A-V Delay interval, which intervals are then displayed in a scaled manner, as part of a time-bar display, as above-described.

For the situation shown in FIG. 9B, there is no spontaneous cardiac activity before the termination of the A-V Delay interval. Hence, the pacemaker generates a ventricular pulse at the conclusion of the A-V Delay (i.e., 165 msec after the atrial pulse for the programmed values shown in FIG. 9B). This ventricular pulse is manifest in the intercardiac ventricular channel display 338 as a large negative-going pulse 346, and may also be manifest in the atrial channel display 336 as a far-field spike 348. A "V" marker 350 is also generated on the display, as is a long vertical line 352 that marks the beginning of the PVARP, VRP, MAX Track, and Rate programmed intervals that are included in the display of the time bar portion 334. Advantageously, the display of these time intervals in a scaled time diagram that also includes the intercardiac ECG channel(s), provides an extremely useful tool for diagnosing the intercardiac waveform and for analyzing the performance of the pacemaker, and for determining whether the pacemaker has been optimally programmed. Never before, to Applicants' knowledge, has a programming device been capable of generating a display of the type shown in FIG. 9B that includes such valuable timing and other information relating to the presently programmed intervals and corresponding intercardiac ECG waveform(s).

Submitted herewith as Appendix C is a representative program listing of the software that is used to generate and control the interval programming features of the present invention. This program listing is liberally annotated with comment statements, and is believed to be self-explanatory to those skilled in the pacemaker and programming arts. Hence, one skilled in the art, given the descriptions of interval programming presented herein, and including the program listings of Appendix C, could readily implement and practice the present invention.

While the invention described herein has been described with reference to a particular embodiment and application thereof, numerous variations and modifications could be made thereto by those skilled in the art without departing from the spirit and scope of the invention as claimed. Accordingly, the true scope of the invention should be determined with reference to the claims set forth below.

What is claimed is:

1. An analyzer programmer system for controlling and monitoring an implantable programmable pacemaker, said pacemaker having means for receiving control signals and means for transmitting data signals, said analyzer programmer system comprising:
   telemetry head means for noninvasively sending control signals to said pacemaker and for noninvasively receiving data signals form said pacemaker;
   processing means coupled to said telemetry head means for generating said control signals in response to selected commands entered into said system, and for processing said data signals received from said telemetry head means;
   memory means coupled to said processing means for storing said data signals; and
   electronic display means for displaying the information contained within said data signals and said control signals, said display means including means for electronically displaying a plurality of graphically depicted programmed intervals, said graphically depicted programmed intervals including a graphical indication of the starting point and duration of selected time intervals included within a graphical representation of a predefined cycle associated with the operation of said programmable pacemaker, said selected time intervals being specified in the control signals sent to said pacemaker.

2. The analyzer programmer system of claim 1 wherein said control signals control at least the programmed duration of selected time intervals used during operation of said pacemaker, and said data signals include at least the measures duration of selected time intervals associated with the operation of said pacemaker, and further wherein the programmed intervals graphically displayed by said electronic display means comprise a scaled graphical diagram of predicted time intervals within said predefined pacemaker cycle that results from the sending of the control signals to said pacemaker and the acting upon said control signals by said pacemaker.

3. The analyzer programmer system of claim 2 wherein said display means further includes means for simultaneously displaying the programmed time intervals of said electronic display means and the measured time intervals derived form said data signals, thereby facilitating a comparison between that which is predicted and that which is measured.

4. A time interval programming system for controlling and monitoring an implantable pacemaker, said implantable pacemaker including means for receiving commands, said time interval programming system comprising:
   means for transmitting commands to the receiving means of said implantable pacemaker, said commands including the programmed duration of selected time intervals associated with the operation of said implantable pacemaker; and
   means for graphically displaying selected time intervals included in said commands in a visual representation that depicts when, within a graphical depiction of a predefined cycle associated with the operation of said implantable pacemaker, each displayed time interval begins and ends.

5. The time interval programming system of claim 4 wherein said implantable pacemaker further includes means for sensing and generating events, and means for transmitting data signals representative of said events, and wherein said time interval programming system further includes means for receiving said data signals, and wherein said graphical display means includes data display means for simultaneously displaying events sensed and generated by said implantable pacemaker in a timed relationship aligned with the display of said time intervals, said data display means showing the events thus displayed in timed relationship relative to said predefined cycle.

6. The time-interval programming system of claim 4 wherein the implantable pacemaker is a dual chamber pacemaker and wherein the time intervals displayed by said graphical display means include programmed atrial and ventricular refractory periods and a programmed A-V delay interval associated with the operation of the dual chamber pacemaker.

7. In an analyzer programmer system for use with an implantable pacemaker, said system including processing means for carrying out specific instructions associated with a particular type of implantable pacemaker; a removable program cartridge wherein said specific instructions are stored; a data bus connecting said processing means with said program cartridge, and over which data bus said specific instructions are transferred to said processing means from said program cartridge; and an address bus, also connecting said processing means with said program cartridge, and over which address bus a data address signal is provided to said program cartridge from said processing means; a memory access system within said program cartridge comprising:
   multi-page memory means within said program cartridge for storing the specific instructions at one of a plurality of possible pages, said multi-page memory means including access means for accessing a specific location within said memory means that includes means for specifying a desired page where desired data is located, and means for subsequently specifying where on the desired page the desired data is located, whereby at least two consecutive instructions may be used to retrieve data from said multi-page memory means: a first instruction to specify the page, and a second instruction to specify where on the specified page the desired data is located; and
   decoding means responsive to the receipt of a single data address instruction received over said address bus for decoding said single data address instruction and for placing the data at the specific location designated by the decoded single data address instruction on said data bus for presentation to said processing means, said decoding means accomplishing its function of retrieving the addressed data without the need for consecutive plural instructions specifying first the page and second the location on the page where the data is located whereby data can be retrieved from said multipage memory means using a single memory instruction.

8. The memory access system of claim 7 wherein said decoding means includes means for coupling a selected portion of said address bus directly to said data bus.

9. A memory access system for a read-only memory (ROM) subsystem of a microprocessor-controlled programmer system, said microprocessor-controlled programmer system being used for programming a medical device, said microprocessor-controlled programmer system having means for generating a clock signal, said clock signal defining a basic clock cycle, said clock signal being applied to said ROM subsystem to control the retrieval of data stored therein, said ROM subsystem including a plurality of commercially available ROM devices that have been programmed with specified data, said ROM devices being configured to organize the specified data into a plurality of pages, and said ROM devices typically requiring two consecutive memory instructions, executable over at least two consecutive basic clock cycles, in order to retrieve a selected portion of the specified data stored in said ROM devices: a first instruction to specify a page, and a second instruction to specify where on the specified page the selected portion of the specified data is located; the improvement of said memory access system comprising:

address means fo generating a single memory address instruction that specifies the location within said ROM where the selected portion of the specified data is stored;

means for applying said single memory address instruction to said ROM subsystem; and decoding means within said ROM subsystem responsive to said single memory address instruction for retrieving the selected portion of the specified data from said ROM devices within a single basic clock cycle.

10. The memory access system of claim 9 wherein said decoding means comprises a programmed logic array (PAL) device that includes:

means for receiving a multi-bit address instruction; and means responsive to the individual its of said multi-bit address instruction for immediately generating, without waiting for the beginning of the next basic clock cycle, a set of appropriate control signals that cause the selected portion of the specified data to be retrieved from said ROM devices.

11. A method of analyzing the ECG signals sensed by an implantable cardiac pacemaker, said pacemaker having a plurality of specified time intervals associated with its operation, said method comprising the steps of:

(a) sending control signals to said implantable cardiac pacemaker that indicate the duration of said specified time intervals;

(b) electronically displaying a first time-scaled graphical display that displays a representation of said specified time intervals in graphical form;

(c) receiving ECG signals from said cardiac pacemaker that indicate various cardiac events sensed by said pacemaker; and (d) electronically displaying a second time-scaled graphical display that graphically displays the occurrence of said sensed cardiac events.

12. The analyzing method of claim 11 wherein the electronic first and second time-scaled displays are displayed simultaneously, thereby facilitating a comparison of the specified time intervals and the measured cardiac events.

13. The analyzing method of claim 11 wherein the specified time intervals displayed in said first time-scaled display include an A-V interval and a rate interval.

14. The analyzing method of claim 11 wherein step (6) comprises displaying said specified time intervals as a horizontal bar chart, the horizontal axis of said bar chart comprising a time axis, each time interval being represented as a separate bar on said bar chart that begins and ends at an appropriate location along said horizontal axis.

* * * * *